(12) United States Patent
Hegemann

(10) Patent No.: US 7,059,853 B2
(45) Date of Patent: Jun. 13, 2006

(54) ORAL IRRIGATION AND/OR BRUSHING DEVICES AND/OR METHODS

(75) Inventor: Kenneth J. Hegemann, Escondido, CA (US)

(73) Assignee: CRA Labs, Inc., Escondido, CA (US)

( * ) Notice: Subject to any disclaimer, the term of this patent is extended or adjusted under 35 U.S.C. 154(b) by 54 days.

(21) Appl. No.: 10/357,564

(22) Filed: Feb. 5, 2003

(65) Prior Publication Data

US 2004/0072122 A1 Apr. 15, 2004

Related U.S. Application Data

(60) Provisional application No. 60/409,760, filed on Sep. 10, 2002, provisional application No. 60/403,915, filed on Aug. 15, 2002, provisional application No. 60/385,366, filed on Jun. 3, 2002.

(51) Int. Cl.
*A61C 17/00* (2006.01)
*A61C 5/00* (2006.01)
*A61H 7/00* (2006.01)
*A46B 9/04* (2006.01)

(52) U.S. Cl. .................. 433/80; 433/140; 601/163; 132/322; 15/167.2

(58) Field of Classification Search ............... 433/140, 433/80, 82, 87; 15/167.1, 167.2; 601/162, 601/163, 164; 132/322; 239/154, 550, 551
See application file for complete search history.

(56) References Cited

U.S. PATENT DOCUMENTS

| | | | |
|---|---|---|---|
| D48,666 S | 3/1916 | Boccia | |
| D53,715 S | 8/1919 | Samson | |
| 1,679,946 A | 8/1928 | Ruff | |
| 1,830,995 A | 11/1931 | Genn | |
| 1,908,509 A | 5/1933 | Davis | |
| 2,093,383 A | 9/1937 | Rudof et al. | |
| 2,528,992 A | 11/1950 | Barr | |
| 2,682,066 A | 6/1954 | Keely | |
| 2,771,624 A | 11/1956 | Ripper | |
| 2,807,820 A | 10/1957 | Dinhofer | |
| 3,178,754 A | 4/1965 | Cleverdon | |
| 3,227,158 A | 1/1966 | Mattingly | |
| 3,241,239 A | 3/1966 | Ellis | |
| 3,284,829 A | 11/1966 | Allen | |
| 3,393,673 A | 7/1968 | Mattingly | |
| 3,425,410 A | 2/1969 | Cammack | |
| 3,453,969 A | 7/1969 | Mattingly | |
| 3,465,751 A * | 9/1969 | Powers | ........................ 601/162 |
| 3,467,083 A | 9/1969 | Mattingly | |
| 3,623,175 A | 11/1971 | Emerson | |
| 3,732,589 A | 5/1973 | Burki | |
| 3,742,942 A * | 7/1973 | Westline | ...................... 433/216 |
| 3,753,435 A * | 8/1973 | Blasnik | ...................... 601/163 |
| 3,878,577 A | 4/1975 | Jousson | |
| 3,935,971 A * | 2/1976 | Papoff et al. | ................ 222/134 |

(Continued)

FOREIGN PATENT DOCUMENTS

CH 179403 9/1935

(Continued)

*Primary Examiner*—Todd E. Manahan
(74) *Attorney, Agent, or Firm*—Hensley Kim & Edgington LLC; Peter B. Scull

(57) ABSTRACT

An oral hygiene device having, in one embodiment, a unique, peristaltic pump water streaming or jet action; and in another embodiment, a multi-headed toothbrush may also be disposed on the end of a handle on which the jet nozzle or nozzles are disposed.

16 Claims, 36 Drawing Sheets

U.S. PATENT DOCUMENTS

| | | |
|---|---|---|
| 3,937,582 A | 2/1976 | Del Bon |
| 3,953,907 A | 5/1976 | Froidevaux |
| 3,984,890 A | 10/1976 | Collis |
| 4,048,690 A | 9/1977 | Wolfson |
| 4,060,870 A * | 12/1977 | Cannarella ............ 15/24 |
| 4,071,956 A | 2/1978 | Andress |
| 4,108,167 A | 8/1978 | Hickman et al. |
| 4,141,352 A | 2/1979 | Ebner et al. |
| 4,146,020 A | 3/1979 | Moret et al. |
| 4,223,417 A | 9/1980 | Solow |
| 4,225,994 A | 10/1980 | Stoltz |
| 4,302,186 A | 11/1981 | Cammack et al. |
| 4,346,492 A | 8/1982 | Solow |
| 4,498,269 A | 2/1985 | Weiss |
| 4,534,340 A | 8/1985 | Kerr et al. |
| 4,766,630 A | 8/1988 | Hegemann |
| 4,795,347 A | 1/1989 | Maurer |
| 4,989,590 A | 2/1991 | Baum et al. |
| D315,450 S | 3/1991 | Wagner |
| 5,000,684 A | 3/1991 | Odrich |
| 5,036,562 A | 8/1991 | Reynolds |
| 5,062,413 A * | 11/1991 | Bullard ............ 601/162 |
| 5,068,939 A | 12/1991 | Holland |
| 5,148,567 A | 9/1992 | Daub |
| 5,177,826 A | 1/1993 | Vrignaud et al. |
| 5,199,604 A | 4/1993 | Palmer et al. |
| 5,208,933 A | 5/1993 | Lustig et al. |
| D339,692 S | 9/1993 | Schneider |
| 5,253,382 A | 10/1993 | Beny |
| 5,259,083 A | 11/1993 | Stansbury, Jr. |
| 5,305,491 A | 4/1994 | Hegemann |
| 5,316,027 A | 5/1994 | Klinkhammer |
| 5,327,607 A | 7/1994 | Wagner |
| 5,342,196 A * | 8/1994 | Van Hale ............ 433/82 |
| 5,406,664 A | 4/1995 | Hukuba |
| 5,407,254 A | 4/1995 | Hegemann |
| 5,443,386 A | 8/1995 | Viskup |
| 5,497,526 A | 3/1996 | Klinkhammer |
| 5,570,709 A | 11/1996 | Haddad et al. |
| 5,593,304 A | 1/1997 | Ram |
| 5,669,097 A | 9/1997 | Klinkhammer |
| 5,673,454 A | 10/1997 | Quintanilla et al. |
| D385,702 S | 11/1997 | Okada |
| D386,315 S | 11/1997 | Vrignaud |
| 5,733,117 A | 3/1998 | Coss et al. |
| 5,758,380 A | 6/1998 | Vrignaud |
| RE35,941 E | 11/1998 | Stansbury, Jr. |
| D401,414 S | 11/1998 | Vrignaud |
| D401,415 S | 11/1998 | Vrignaud |
| D401,416 S | 11/1998 | Vrignaud |
| D401,417 S | 11/1998 | Vrignaud |
| D401,418 S | 11/1998 | Vrignaud |
| 5,853,290 A | 12/1998 | Winston |
| 5,934,762 A | 8/1999 | Vrignaud |
| 5,947,729 A | 9/1999 | Bell |
| 6,019,905 A | 2/2000 | Waggoner |
| 6,152,733 A | 11/2000 | Hegemann et al. |
| 6,203,320 B1 | 3/2001 | Williams et al. |
| 6,233,773 B1 | 5/2001 | Karge et al. |
| 2003/0013063 A1* | 1/2003 | Goldman ............ 433/80 |

FOREIGN PATENT DOCUMENTS

| | | |
|---|---|---|
| DE | 4115943 | 11/1991 |
| EP | 0611533 | 8/1994 |
| EP | 865770 A1 * | 9/1998 |
| FR | 588348 | 5/1925 |
| FR | 855253 | 5/1940 |
| FR | 881678 | 5/1943 |
| FR | 911243 | 7/1946 |
| FR | 2618651 | 2/1989 |
| FR | 2641680 | 7/1990 |
| GB | 2192784 | 1/1988 |
| WO | WO 80/00909 | 5/1980 |
| WO | WO 89/01303 | 2/1989 |

* cited by examiner

ORAL IRRIGATION AND/OR BRUSHING DEVICES AND/OR METHODS

This application claims the benefit of provisional applications Nos. 60/385,366 filed Jun. 3, 2002; 60/403,915 filed Aug. 15, 2002; and 60/409,760 filed Sep. 10, 2002 now abandoned.

INTRODUCTION

The present invention relates generally to oral irrigation devices and/or power tooth and gum cleansing devices and/or power toothbrushes and more particularly, in some embodiments, to a pressure pump for an oral irrigation device and/or to a method of using the same, and in other embodiments, to a system for moving one or more cleaning (irrigation and/or brushing) heads during use. The general purpose may include providing one or more pressurized water streams that may pulsate and may be adaptable to having injected therein water and/or dentifrice, flavoring, or medicine or the like. Another purpose together with or in lieu of pulsatile action may be providing reciprocal cleaning head movement in the user's mouth. These embodiments may be particularly useful with a toothbrush or like arrangement which assists in guiding the cleansing heads within the user's oral cavity to aid in proper cleansing and stimulation to enhance healthy teeth and gums.

BACKGROUND

Over the years, a diverse array of manual and automated tooth cleansing devices have been developed including electric toothbrushes, oral irrigators and flossers and many have enjoyed widespread commercial success. These have been generally directed at the important basic need to clean the teeth, gums and certain parts or the whole of the mouth area.

Nonetheless, many deficiencies remain with various of these devices, and for many people and in many situations, they are inadequate or unsuitable. Manual brushes, for instance, require the user to have a minimum, moderate degree of manual dexterity and the ability to firmly grasp the brush while moving it against the dental surfaces. The tiresomeness, difficulty and repetitiveness of manual brushing leads many to do less than is necessary; as was reported in Consumer Reports, September 1992, page 611: "People tend to brush for less than a minute. You need two or three minutes of manual brushing to do the job right." And thus, some teeth and gum surfaces may receive inadequate brushing or are missed altogether.

An intriguing note is that some statistics show that nearly 75% of the adult population suffers from some form of gum disease, which in turn can lead to tooth loss. The primary cause of gum disease may very well be inadequate gum brushing and massage. This conclusion may be supported in part by the fact that dental professionals (dentists and hygienists) are rarely affected by gum disease and/or tooth loss. Interestingly, they use the same toothbrushes as used by the general population. The reason for this vast difference in oral health can be attributed to the fact that dental professionals (as part of their training) are taught exactly how to brush teeth and gums and most importantly, they comply with these cleaning measures every day. A logical conclusion is that gum disease is likely caused by human error. Additionally, flossing can be mentioned in noting that it has often been found to be a cumbersome, time demanding and sometimes painful way to remedy some of the deficiencies found in the other methods, such as brushing, particularly when attempting to reach areas between the teeth.

Conventional electric or "power" toothbrushes, while requiring less physical effort on the part of the user, still often require human skill and dexterity to achieve effective results. These are often more complicated than manual brushes and are more expensive and require more time in maintenance. Moreover, brushing too vigorously with electric brushes can irritate the gums or cause them to bleed excessively, possibly injuring the gums or eventually causing them to recede. Furthermore, bleeding can spread oral bacteria into the bloodstream, a risk for users with various health conditions including heart and immunity problems. Because of these problems and/or similar drawbacks, children must often be supervised when using electric toothbrushes, and many children probably should not use them at all.

Oral irrigators (often using pulsating jets of pressurized water) and oral syringes (often non-pulsating jets of pressurized water), while of benefit to many users, including those with crowns, implants, braces, or non-removable bridgework (for whom flossing or brushing may be impractical or not possible), can also be ineffective if the water jet is not correctly directed to the area where it may most be needed for oral irrigation and stimulation. This may be a particular problem for an unsuspecting user if there are higher pressures involved which can exacerbate gum or tooth ill health.

Power toothbrushes and oral irrigation devices have been developed in many forms in the art. As a primary example, the WaterPik® oral irrigation device (from WaterPik Technologies, Inc., formerly Teledyne WaterPik, Inc., Fort Collins, Colo., USA) uses a piston pump which generates a high frequency (from about 1000 to about 3000 pulses/minute) water jet. Such a high frequency pulse can be uncomfortable to the user. The B. Braun Company (Braun AG, Frankfurt, Germany) has also developed some successful commercial oral irrigation and/or toothbrush devices. Similarly, sonic or ultrasonic technologies have also been developed and implemented in the art of oral care. Examples are available from the Sonicare Company, also known as Philips Oral Healthcare, Inc., Snoqualmie, Wash., USA (a subsidiary of Royal Philips Electronics, N.V. of the Netherlands) or the Oral B Laboratories company of Boston Mass., USA (the Braun and Oral-B brands and companies being subsidiaries of the Gillette Co., Boston Mass., USA).

A major shortcoming of many conventional manual and electric toothbrushes, oral irrigators and flossing is that they may be dependent on accurate human manipulation in order to achieve effective disease preventing results. The high incidence of gum disease in the general population provides convincing evidence that present means of tooth and gum brushing may be inadequate for most users simply because they depend on human skill. The present invention substantially eliminates the need for human skill. Many prior means and methods are not simply capable of effective operation; hygienic, comfortable, and/or error-free use; easy and inexpensive maintenance; with a cost-effective purchase price, for most people in most situations. Thus, there is a need for an improved device and the present invention fills this need by substantially overcoming many of the foregoing deficiencies.

The present invention is presented as a means to remedy one or more of the above-mentioned defects of past devices and/or methods with the provision of a dental care device which provides a safe, fast, comfortable and effective means of dental care for substantially eliminating gum disease for people of all ages, including those with implants, crowns, braces and bridgework, as well as people of limited dexterity, or other handicaps.

SUMMARY OF THE INVENTION

The present invention provides a dental cleaning appliance for cleaning teeth and gums having one or more jet nozzles on or forming one or more cleaning heads which is/are insertable into the user's mouth for the cleaning operation, the cleansing head or heads being attached to a handle, which is attachable via one or more fluid tubing lengths to a power pump module which activates either one or more jet nozzles by pumping water thereto. The tubes provide a connection from a fluid source to and/or through the pump and thence to and through the handle and nozzles. In yet another embodiment, the present system can provide for simultaneously delivering a controllable supply of customized dentifrice and/or mouthwash and/or medicine as may be desired by the cleansing operation for any user's unique situation.

One or more peristaltic pumps may be used in one embodiment herein and may be rotated at various speeds and thereby generate more desirable pulse frequencies (for example, at speeds which can generate approximately 250 pulses per minute) than a piston pump. Moreover, stacked peristaltic pumps with alternating rotors may provide alternating water pressures, and alternating water jets. Still furthermore, a third stage peristaltic rotor can be stacked therewith to provide the injection pressure for delivering flavors, dentifrices, medicines and/or the like to the water stream or streams.

Thus disclosed herein are means, structures and methods for pressurizing water for an oral irrigation device which in some embodiments involve one or more pressurized water jets, along with an optional means of injecting concentrated dentifrice and/or flavors and/or medicine into the pressurized water stream. As mentioned, a general purpose may be in providing a water stream that pulsates and is adaptable to have injected therein a dentifrice, flavoring, or medicine into the pressurized stream of water. In one embodiment, this may be accomplished through use of a peristaltic pump or pumps to generate the pressure, flow, and desired pulsating action of one or more water jets. It may also include using a dentifrice peristaltic pump to meter in the correct amount of dentifrice, flavor, or medicine.

In a more detailed description of one of many preferred options, the present cleansing device may have two (2) water jet nozzles for the top teeth and/or, in a further embodiment, two (2) more jet nozzles for the bottom teeth which may provide definite discrete pulses for intermittently jetting water between teeth, which in one embodiment may include providing a first pulse in one direction, e.g., inwardly toward the tongue, and a second jet pulsating in a second, generally opposed direction, e.g., outwardly toward the cheek, and so on repetitively so that the jet action may remove matter from between teeth.

A two (2) stage peristaltic pump, in one embodiment involving stacked peristaltic pumps with alternating rotors as yet unknown to oral hygiene devices, may be used to provide this alternating intermittent pulsing of water jets. In one embodiment, each peristaltic pump stage may have only a single roller so that each revolution of the pump may generate respective pulses, one for inward pressure and one pulse for outward pressure. The respective singular rollers may then also provide relative timing so that one pulse follows the other. This sort of pump may then provide pulsating water jets that are highly effective at removing debris yet remaining very comfortable to the user. As mentioned, an embodiment of the present invention may involve "stacking" two such peristaltic water pumps in such a manner as to get the automatic alternating pulse action and have this provided in a relatively small package. Also, by stacking the pumps, this assures a sort of perfect pulse "timing" since the two pumps can be run on a common shaft and may then be powered by a common motor. Each pump in the "stack" can have a single roller. The respective singular rollers of the two pumps can then be positioned offset 180 degrees in relation to each other. When the common motor shaft makes one-half of a revolution, the first pump delivers one pulse of water to one of the delivery tubes. When the motor completes the other one-half revolution, the other pump delivers a pulse of water. This is one way in which the pulses can be "timed." It should also be understood that the reason the water may desirably be delivered in pulses from each pump is that a single roller on the tube of each pump is in contact with the tube only during one-half of a complete revolution since the tube in contained in a half circle raceway, not a complete circle. When the roller in not in contact with the tube, there can be a moment of water relaxation (no pressure) and as soon as the roller comes in contact with the tube, pressure is applied. Pressure can be a result of resistance, and resistance may be obtained by controlling the resilience of the tubing and by sizing the water jet nozzles in the cleansing head correctly (small enough to create enough resistance to obtain the desired water pressure).

Moreover, this pulsing action provided by such a two (2) stage pump may also be used with a novel means of automatically positioning the water jets most advantageously or correctly in the oral cavity adjacent the teeth. This may take the form of one or more brush heads or other devices such as a bite block or like guide device.

Further in another embodiment, it may also be desirable to provide a structure and method of injecting flavor concentrate, dentifrice, or the like, into the water stream. To provide such optional flavor or dentifrice injection, a third pump may be used simultaneously with the other water pump or two stage pumping, to inject this other substance (flavor, dentifrice, medicine or the like) into the water stream or streams. This sort of injection pump may deliver concentrate at a much lower rate than the water pump or pumps. It has been found that a favorable ratio may be about 100 to 1 (water to concentrate).

In still more detail of another embodiment hereof, a reservoir cup can be used to provide water for feeding to the pump. The water can be drained to the pump, first through a common conduit which can then be split at a Y-connection (or the like) to feed the two discrete stages of the pump. Then, as the two stage pump rotates, a one-half revolution may deliver one (1) pulse or jet of water to the water jet/nozzle device pointing in a first direction (e.g., inwardly); and then a further one-half revolution of the two stage pump may then deliver another single pulse or jet of water to a second jet/nozzle device which is pointing in a second direction (e.g., outwardly). Then, with further rotations of the pump heads, this alternating intermittent pulsing can continue, first one jet in one direction, then a second jet in the second direction, and so on, as introduced above. The first and second directions may be generally opposed to each other, however, they need not be directly opposed. Rather, even if one jet is directed generally inwardly, and the other generally outwardly, the two corresponding jets may also be relatively angularly disposed (up or down or laterally or both) and thus not be directly opposed to each other.

The cleansing handle includes a cleansing head which may have one, two or more water jets, and in one embodiment includes two (2) jets fed by two (2) discrete tubes and in another embodiment includes four (4) water jets that are fed primarily by two (2) tubes, which may be split into four (4) water tubes. These ultimate four tubes receive water from two supply tubes that connect the power handle to the pump module. When one of the two tubes receives a pulse of water from the two stage pump, it is delivered up to the handle where it is split into two of the water tubes that feed two of the water jet nozzles. These two jets can then substantially simultaneously spray water from the one side, e.g., the outside (cheek side) toward the inside (tongue side). When the other tube receives a pulse of water from the two stage pump, it can be delivered up to the handle where it may be split into the other two water tubes to feed the other two water jet nozzles. These other two jets can then substantially simultaneously spray water from the other side, e.g., inside (tongue side) toward the outside (cheek side). There may be a very definite pulse factor involved that provides first a pulse of water from the outside, then a pulse from the inside. It has been found that between about 100 and about 500 pulses, and in one embodiment approximately 250 pulses per minute may provide the most effective results. The alternating pulse (out-to-in then in-to-out) etc. can be very desirable because in the alternative where the pulses may be at the same time, debris could get trapped between the coinciding pulses between the teeth essentially at the mid point between the teeth. Alternating pulses allows for the possibility of each pulse of water to flush debris completely away since the water stream may be allowed to go all the way through the tooth space before the opposing pulse of water squirts in the opposite direction. As mentioned, to get two streams of water that independently pulsate, two pumps or a two stage pump may be used. These two pumps or two stages may be located within the pump module, and as described, if "timed" accurately relative to each other they can ensure accurately alternating pulses of water.

A dentifrice injection pump may also be "stacked" on the same shaft as one or more of the water pumps or on the two stage peristaltic pump shaft to make everything compact and inexpensive but this third pump (the dentifrice injection pump) should be geared down in speed relative to the water pump or pumps or driven by a separate motor. A good reason for this involves either the much reduced rate of dentifrice injection (e.g., 100 to 1) as introduced above, and/or the more constant, less or non-pulsating injection potentially preferred for this flow. (Note, a single pulse pump may alternatively be used.) In any event, for the purpose of this specification, it could be understood as being either powered by the same motor as the water pump or pumps but with a substantial speed reduction and/or tube size reduction or both; or it could simply be powered with a discrete motor, even if it may be made to reside on and/or revolve about the same axle.

Peristaltic pump advantages include a complete flow through system, through which the flowing liquid does not come into contact with any moving parts, and if there is any contamination it flows right through the tube. Moreover, peristaltic pumps may provide for less required maintenance than a piston pump, with fewer moving parts, and less chance of hard water deposits to clog the tube.

In one embodiment the cleansing head on/in which the nozzles may be disposed may further include one or more brushing heads and one or more brushing arms, the one or more brushing heads being reciprocable in one embodiment, and also being disposed so as to include in another embodiment a set of upper brushes and a set of lower brushes, each of said sets of upper and lower brushes being reciprocable in yet another embodiment in alternating opposing disposition to each other. Such brush heads could be used to definitively establish the position of the nozzles in the user's mouth and maintain this position so that it effectively directs the nozzles to jet the water directly at the gum line (or elsewhere, if desired) as may be most appropriate of cleaning and improving oral health. Similarly, a guide member or members such as one or more bite blocks could be used in addition to or in lieu of brush heads to align the nozzles to appropriately direct the water jets in the user's mouth.

In another embodiment the cleansing head or heads on/in which the nozzles may be disposed may further be movable the one or more cleansing heads being reciprocable in one embodiment. Moreover, the cleansing heads may include one or more brushing heads and one or more brushing arms, the one or more brushing heads being reciprocable in some embodiments and in some being reciprocable with or counter the nozzle heads. These may also be disposed so as to include in another embodiment a set of upper brushes and a set of lower brushes, each of said sets of upper and lower brushes being in some embodiments reciprocable, and in yet another embodiment being reciprocable in alternating opposing disposition to each other. Such brush heads could be used to definitively establish the position of the nozzles in the user's mouth and maintain this position so that it effectively directs the nozzles to jet the water directly at the gum line (or elsewhere, if desired) as may be most appropriate of cleaning and improving oral health. Similarly, a guide member or members such as one or more bite blocks could be used in addition to or in lieu of brush heads to align the nozzles to appropriately direct the water jets in the user's mouth.

Accordingly, an aspect of the present invention is to provide a new and improved oral cleaning device including one or more jet nozzles which may be positioned by a cleansing head and spray assembly in a substantially pre-selected position and a pump module to induce water jetting for cleaning and massaging of the user's teeth and gums. Another aspect of the present invention may be to provide a new and improved oral cleaning device including one or more jet nozzles which are disposed on or adjacent a brush head assembly such that the nozzles may be accurately positioned by or with assistance of the brush head assembly in a pre-selected disposition and a pump module to provide for accurate brushing, cleaning and massaging of the user's teeth and gums.

Still another aspect of the present invention may be to provide a new and improved oral cleaning device including one or more jet nozzles which are disposed in adjacency with a guide or bite block assembly which provide assistance in accurately positioning the nozzles in a pre-selected disposition to induce accurate cleaning and massaging of the user's teeth and gums.

Another aspect of the present invention may be to provide a new and improved device in which the parameters of a user's brushing needs are substantially automatically accounted for any user such that jet nozzles selectively transmit water through the cleansing head to activate the tooth and gum cleansing process in a water jet pattern (direction and angle) meeting the needs of any user while substantially eliminating human error.

And yet another aspect of the present invention may be to provide a new and improved device in which one or more jet nozzles may be moved such that jet nozzles selectively transmit water through the cleansing head to activate the tooth and gum cleansing process in a moving water jet pattern (direction and angle) meeting the needs of any user while substantially eliminating human error.

Yet another aspect may be the provision of a peristaltic pump unit having at least one roller pump to provide pulsating water jet action for cleaning and massaging a user's teeth and gums.

Yet still another aspect may be the provision of a peristaltic pump unit having at least two roller pumps to provide alternating pulsating water jet action for cleaning and massaging a user's teeth and gums.

Yet still one further aspect may be the provision of a peristaltic pump unit having at least one roller pump to provide injection of a dentifrice, flavoring medicine or the like into a water stream pumped to a user's mouth for cleaning and massaging a user's teeth and gums.

A yet still further aspect may be the provision of an piston pump unit having at least one and in another embodiment two chambers for receiving a fluid to be pumped to provide pulsating water jet action for cleaning and massaging a user's teeth and gums.

A still further aspect of the present invention may be the provision of a new and unique oral cleaning device which enables even the physically disabled to assure proper hygiene within his/her oral cavity including teeth, palates, gums, tongue and cheeks once the cleansing head is properly installed without further need of cumbersome hand manipulation.

These and still further aspects as shall hereinafter appear are readily fulfilled by the present invention in a remarkably unexpected manner as will be readily discerned from the following detailed description of exemplary embodiments thereof especially when read in conjunction with the accompanying drawings in which like parts bear like numerals throughout the several views.

DETAILED DESCRIPTION

The present invention relates in general to a new and useful substantially automated oral cleaning device comprising various unique coactive assemblages of several distinct sub-assemblies which will be herein described in some detail. More particularly, the present invention is directed to a plurality of elements which when considered as one or more ensembles, may provide comprehensive attainment and maintenance of oral cleanliness. Of these, there are several primary features; among which are alternative streaming and pulsing water jet actions which in several embodiments may be peristaltically powered.

The present invention relates to an automated tooth and gum cleaning device 20 which includes a pump module 22 and an irrigation unit 24 having a unique nozzle/spray head assembly 26 which may in one or more embodiments also include an optional multiple directional brush head arrangement (herein generally referred to in any of these embodiments as a "cleansing head assembly 26"), which positions the nozzles in operative disposition. The pump control module 22 then provides pumping of water for driving the jet action through the nozzle assembly 26 for cleaning and massaging of the user's teeth and gums. With the use of the optional toothbrush head assemblage, the present invention further provides a totality of brushing, cleaning, massaging and flushing of the user's teeth and gums.

Figure 1:
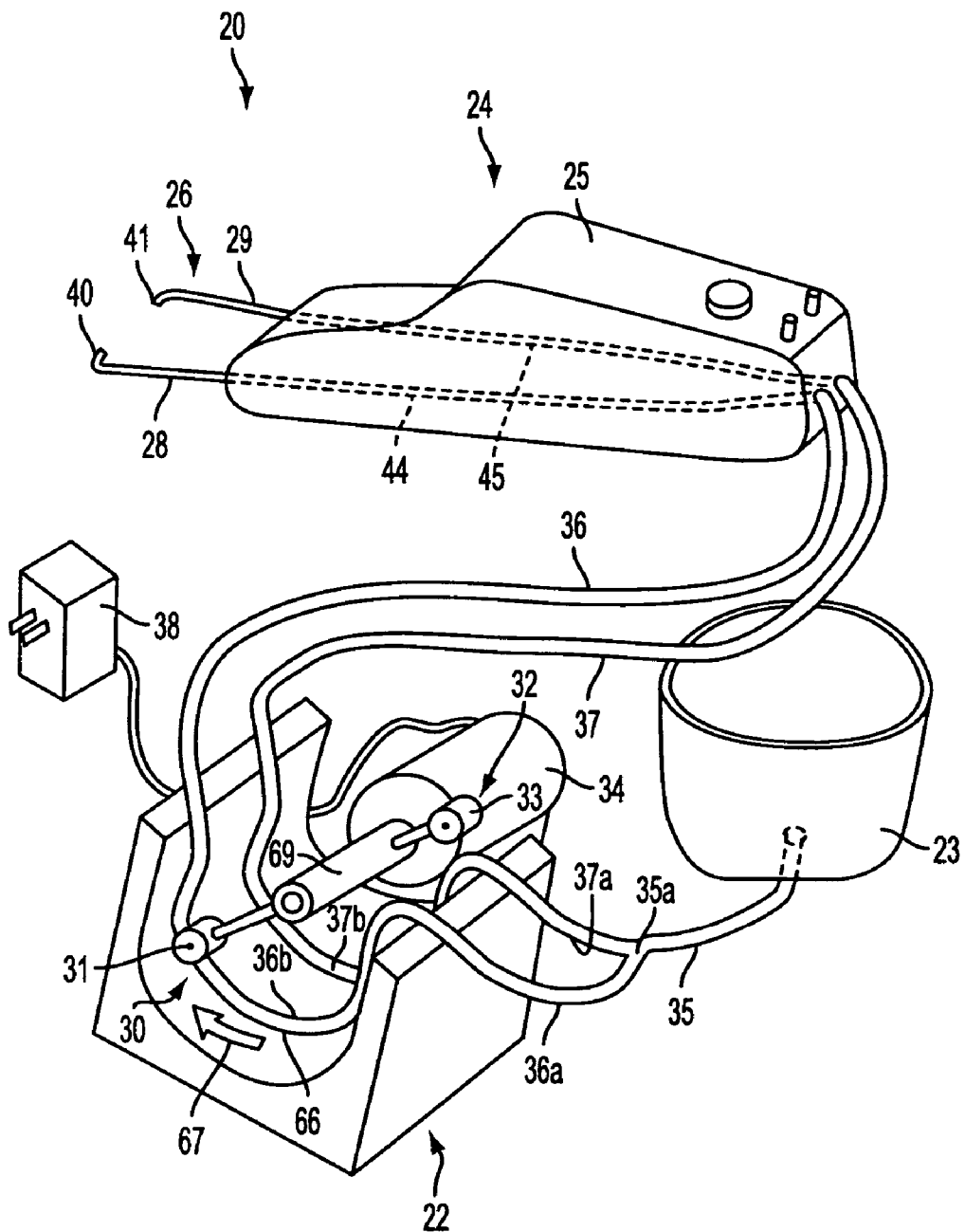
FIG. 1 is an isometric schematic view of an oral hygiene device according to the present invention.
Figure 3:
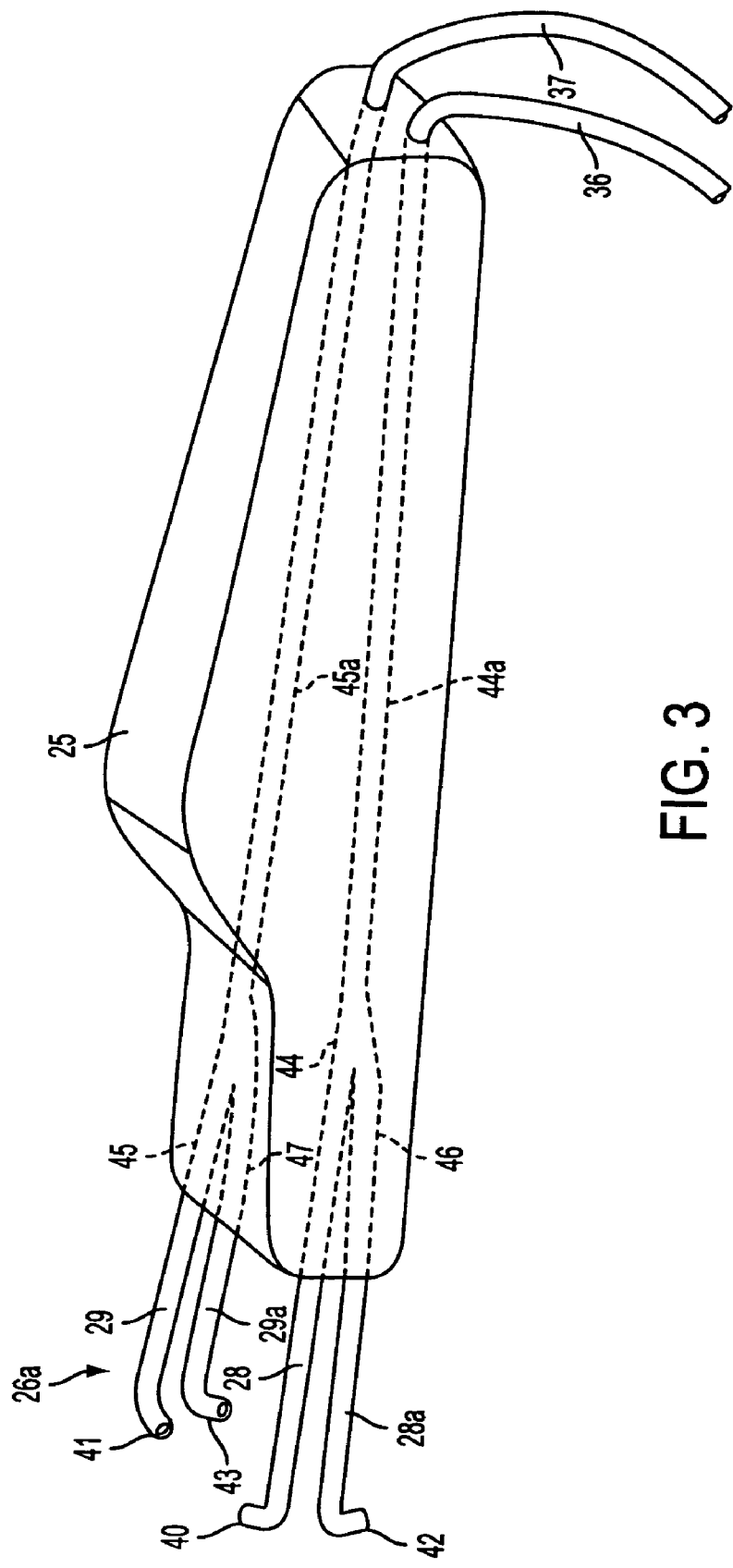
FIG. 3 is an isometric view of an alternative oral hygiene device also according to the present invention.

As will further appear from the below detailed description of the several sub-assemblies hereof in relation to the accompanying drawings, the device 20 may include an irrigation assembly 24 which has one or more jet arms, see e.g., arms 28, 29 in FIG. 1, emanating from the handle support 25, each such arm being capable of having one or more jet nozzles, see e.g., nozzles 40, 41, emanating therefrom. The details of the nozzle mounting and handle support assembly are shown in FIGS. 1 and 3, inter alia. The nozzle heads may be replaceable or interchangeable when and/or if desired.

The action of the nozzle head or heads may be pulsing or merely streaming, and either of these may be delivered from a merely relatively stationary disposition of the nozzle arms and/or nozzle heads, or as is further described below in an alternative embodiment, the nozzle arms and/or heads may be reciprocated in and out (see e.g., FIGS. 17–20, inter alia) as for example could occur in conjunction with the brush heads of FIGS. 4, 5, 7 and 8, e.g. A controlled water stream, whether streaming or pulsing may be delivered at room or tap temperature or alternatively heated to about 90 degrees Fahrenheit, for example (heating not shown). The stream or jets may then be provided to and through the nozzles to wash away the plaque and/or debris dislodged from and between the teeth by the operation of the device as well as providing vital pulsating (or streaming) massage of the gums, particularly between the teeth. Each nozzle unit 24 may be fit for use in any user's mouth for water jet contact of every to-be-cleaned surface of the user's teeth and gums and may provide interproximal, gingival and sub-gingival contact while assuring that the jetting irrigation is not overly aggressive. If dentifrice is desired, it may be injected into and thus flow with the water stream or jets into the user's mouth (see description of FIGS. 4–6, below). In addition, each user may also have his/her own nozzle and/or brush heads for obvious sanitary reasons. As mentioned, and even if replaceable, the nozzle holders may further provide reciprocatable linear movement into and out of the oral cavity in order to adequately reach the rear most teeth and all of those in between.

The pulsing (or streaming) jets are provided by a pump assembly, herein also identified generally as "the pump control module 22" which may include conventional or unconventional pump hardware. When a pump, e.g., pump 30 of module 22 is activated, it provides a water jet spray to the nozzle head assembly 24 for the user. The nozzles are in one embodiment disposed in preselected angular disposition to appropriately impact the teeth and gums and any gaps therebetween at the desired location, height, and width thereof.

Each device may further include a further pump (see e.g., FIGS. 4, 5 and 6, described below) for injecting a flavored dentifrice, medicine or the like into the pulsing jet water stream to enhance the effectiveness of the cleaning and health development and maintenance process.

Further, as introduced above, each device may also include one or more brush heads with the oral irrigator such that the jets may inject water through or adjacent the bristles during a brushing action. Combining brushing and oral irrigation may provide better simulation or replacement of interproximal brushing, flossing, and/or perio picking and/or using proxy brushes.

Positioning the nozzle jets properly may be provided by a guide means which might be one or more bite blocks or one or more brushes themselves that lock around the teeth and correctly position the jets. These alternatives are explored in more detail below.

These advantages and others may be compared to Sonicare and Oral-B/Braun irrigators and power toothbrushes against which devices of the present invention have been clinically testes for removal of plaque and gum tissue repair. Superior results are supported by clinical data as shown by a University of Tennessee study, the Health Science Center, 2002.

Each of the several sub-assemblies will now be described in more detail. Referring again to the drawings, an exemplary oral hygiene device utilizing features of the present invention is shown in FIG. 1 and is identified by the general reference numeral 20 therein. As introduced above, device 20 generally includes a pump module 22, an oral irrigation unit 24 with a handle 25 and an oral irrigation assembly 26. The total assemblage 20 further includes connected to the control module 22, a fluid source 23, first and second pumps 30, 32, a drive motor 34, inlet fluid conduit 35 and one or more outlet fluid conduit or conduits 36, 37 and a power source 38 with a power cord or other transmission connection 39.

A reservoir source 23, here shown generally as a cup 23 can be used to provide water for feeding to the pump or pumps, here pumps 30, 32. The water can be drained to the pump, first through a common conduit 35 which can then be split at a Y-connection 35a (or the like) to feed the two discrete stages of the pump module 22. Here, the Y-connection 35a connects to tube portions 36a, 37a which then feed into tube portions 36b, 37b which are as shown here disposed in operative position in respective pumps 30, 32 where they may be engaged by the respective rollers 31, 33 which pinch/obstruct the tubing portions 36b, 37b and then roll therealong to push fluid therein and therethrough as known in the art of peristaltic pumps generally. Then, as the two stage pumps rotate, a one-half revolution provides for delivering fluid in one tubing portion, e.g., portion 36b to water tubes 44, 45 (shown in dashed lines) disposed inside handle 25. These two tubes 44, 45 may have water supplied thereto from two supply tubes 36, 37 that connect the handle 25 to the pump module 22 that may be made to rest on the counter top or otherwise be disposed in an operative location (neither specifically shown). When one of the two tubes 36, 37, e.g., tube 36 receives a pulse of water from the corresponding pump, e.g., pump 30 here, of module 22, it is delivered up to the handle 25 where it is fed into the corresponding one of the water tubes, e.g., tube 44, that feeds the water jet nozzle 41 through nozzle arm 28. This jet can then spray water from one side of an array of teeth 50, e.g. the outside or cheek side 48 toward the other side, e.g., the inside or tongue side 49 of an array of teeth 50 as shown for example in FIG. 2A.

This corresponding delivery can be substantially simultaneous or alternating to first one conduit, e.g., conduit 36, and then, in a next half revolution of the pumps to provide for delivering fluid in and to the other tubing portion, e.g., portion 37b to the corresponding delivery conduit, e.g., conduit 37. From there, fluid is delivered to the alternate two (2) water jet nozzles 40, 41, that are fed by the two (2) nozzle arms 28, 29 in the handle 25 of the irrigation assembly 24.

Thus when the other extended tube, e.g., tube 37, receives a pulse of water from its corresponding pump, e.g., pump 32 of module 22, this pulse of water may be delivered up to the handle 25 where it can be delivered into the other water tube 45 in handle 25 to feed the other water jet nozzle 41 through arm 29. This jet can then spray water from second side, e.g., the inside or tongue side 49 toward the other side, e.g., the outside or cheek side 48 relative to the array of teeth 50, see FIG. 2A.

Figure 2A:
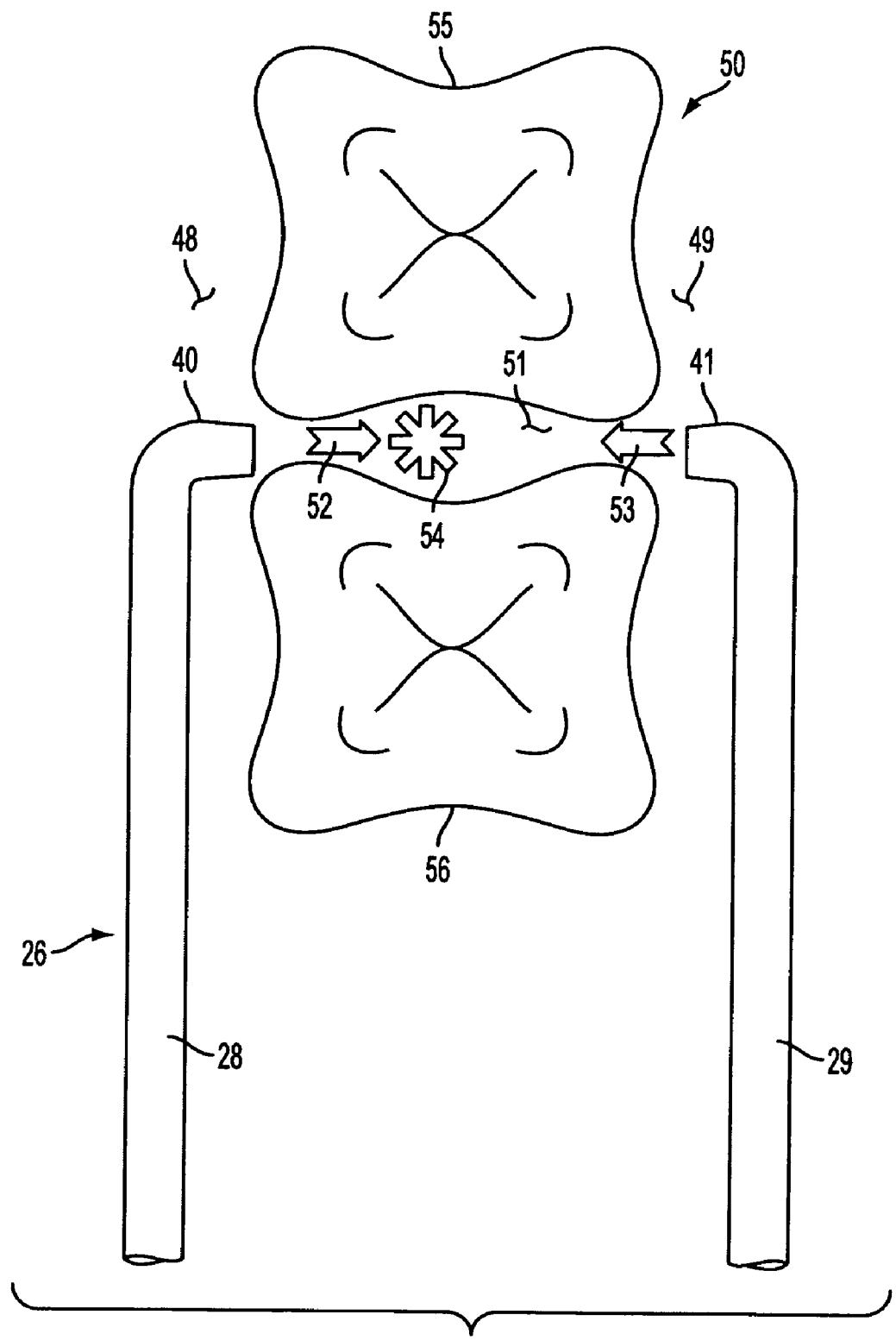
FIG. 2A is a plan view of a cut-away portion of an oral hygiene device of the present invention.

There can then be a very definite pulse factor involved that can provide an alternating arrangement of pulse jets, as shown in FIG. 2A, e.g., a first pulse of water 52 from the outside 48, then a second pulse 53 from the inside 49. It has been found that approximately 250 pulses per minute may provide the most effective results. The alternating pulse (out-to-in then in-to-out) etc. can be highly desirable because a non-alternating set of pulses, e.g., when the pulses are established at substantially the same time, the pulses may then strike substantially simultaneously at debris trapped in the space, e.g., space 51 between the teeth, see e.g., teeth 55, 56, which debris might then be trapped at or near the mid point. Alternating pulses, on the other hand, may allow each pulse of water to separately/independently impact the debris, see particle 54 in FIG. 2A, and thereby loosen the debris more efficiently with a back and forth action (rather than operating to maintain the debris locked in allocation), and thus provide for flushing the debris more completely away. Thus also, in this first embodiment, it can be seen that if timed appropriately, and after all debris is cleared therefrom, the water jet may also be allowed to go all the way through the tooth space before the opposing pulse of water squirts in the opposite direction.

Figure 2B:
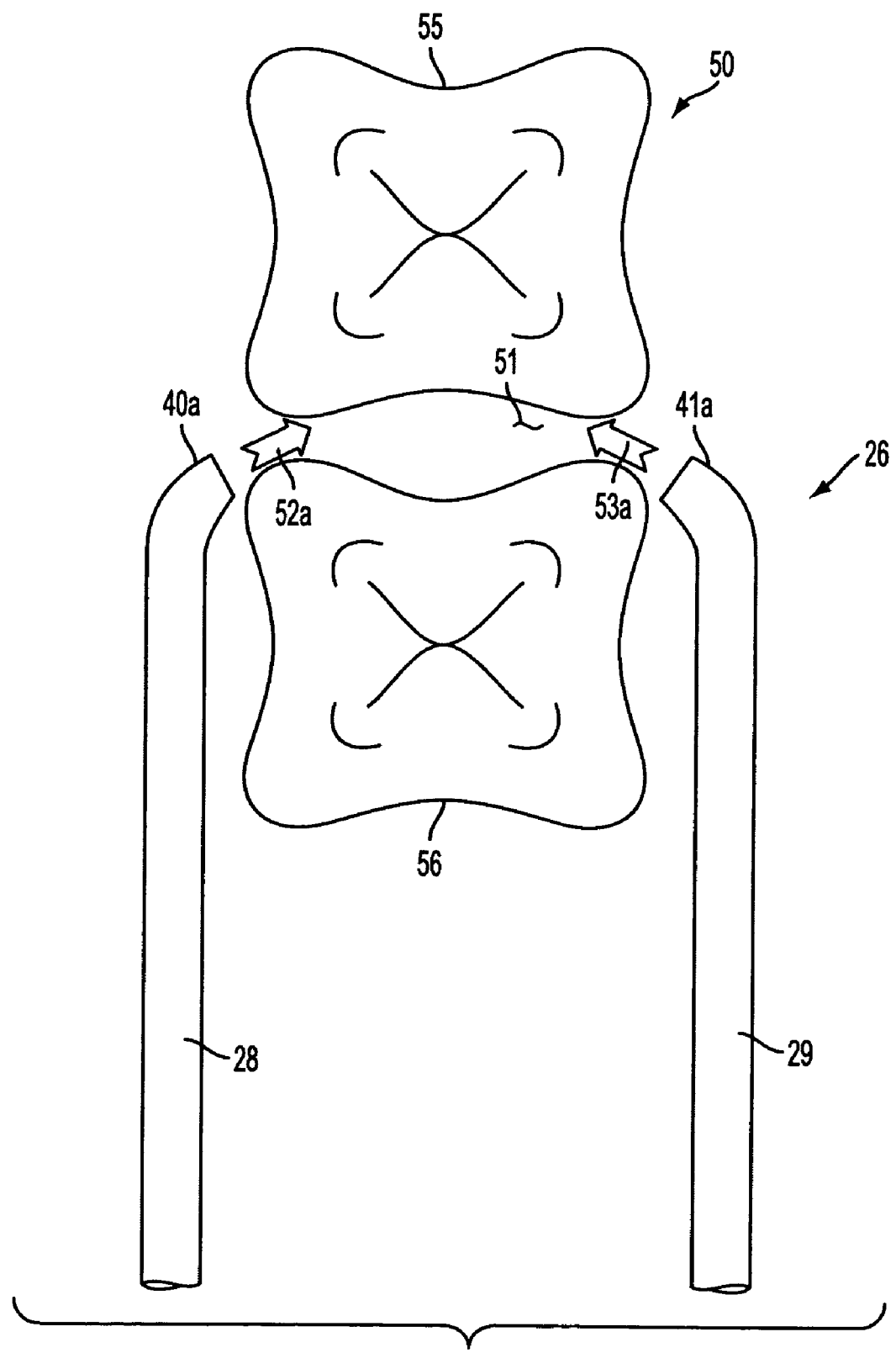
FIG. 2B is a plan view of an alternative cut-away portion of an oral hygiene device of the present invention.
Figure 2C:
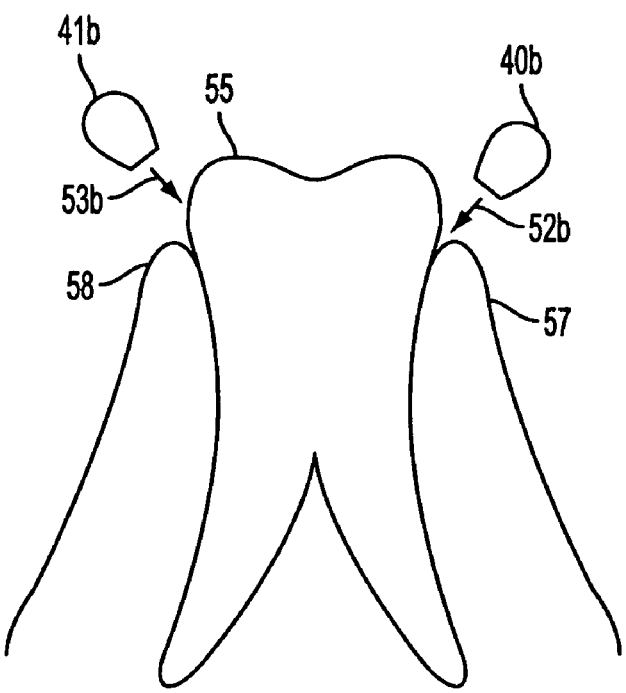
FIG. 2C is an elevational view of a cut-away portion of an oral hygiene device of the present invention.
Figure 2D:
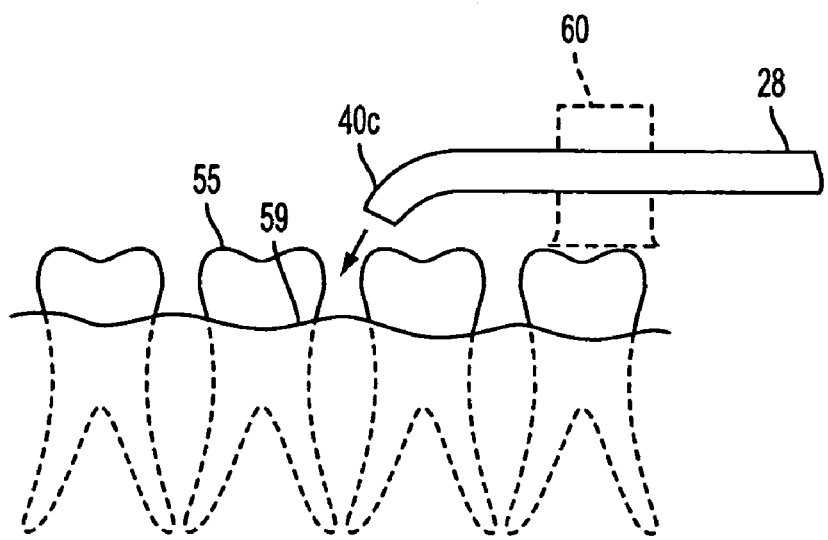
FIG. 2D is another elevational view of a cut-away portion of an oral hygiene device of the present invention.

In a slightly distinct alternative, the nozzles may be disposed so as not to deliver a substantially perpendicular jet action. This is shown for example in FIG. 2B wherein the two nozzle arms 28, 29 have respective nozzles 40a, 41a which are shown delivering respective jets 52a and 53a into the space 51 between teeth 55 and 56. This angular disposition of the nozzle heads 40a, 41a and resultant jets 52a, 53a may provide a desirable jet cleaning action on the respective surfaces of the teeth with which the jets 52a, 53a may more effectively come into contact. A similar set of alternative angular jet dispositions are shown in FIGS. 2C and 2D. Two alternative nozzles 40b, 41b are shown relative to a tooth 55 whereby the respective jets 52b, 53b are shown angled slightly downward to provide a potentially desirable impact of the jets 52b, 53b with the gum line intersection of respective gums 57, 58 with tooth 55. Similarly, a further alternative angled orientation is shown in FIG. 2D wherein an alternative nozzle 40c is shown delivering a jet 52c to a gum line intersection of a tooth 55 with a gum 59. Note, any combination or none of these alternative angular dispositions may be used with the nozzles of the present invention.

In another embodiment (not directly shown), the two tubes 44, 45 can be merged into one tube which can then feed one arm, e.g., arm 28 and thence one nozzle, e.g., nozzle 40, and thereby provide an alternating jet action (first from one tube 36, and then from the other tube 37) to and through one nozzle. Thus, an effective embodiment using only one nozzle is available. Similarly, a single or the two peristaltic pumps could also feed through one or two feed conduits either a substantially continuous stream or pulsating jets to a single nozzle (or multiple nozzles).

As a further alternative embodiment of the present invention, an alternative irrigation assembly 26a is shown in FIG. 3 including a similar handle 25 which here has four (4) water jet nozzles 40, 41, 42, 43 that are fed by four (4) arms 28, 28a, 29, 29a, and four (4) water tubes 44, 45, 46, 47. These four tubes 44–47 may have water supplied thereto from two supply tubes 44a, 45a disposed in handle 25, the supply tubes 44a, 45a receiving water jets from respective conduits 36, 37 which connect the handle 25 to the pump module 22 in the same fashion as shown in FIG. 1 (though not shown in FIG. 3). When one of the two supply tubes, e.g., tube 36 receives a pulse of water from its respective pump 30 of module 22, the water jet is delivered up to the handle 25 where it first delivered to the tube 44a, and may then be split into two of the water tubes, e.g., tubes 44, 46, that feed two of the water jet nozzles 40, 42. These now split jets can then spray water from first one side, e.g. the outside (cheek side) 48 toward the other side, e.g., the inside (tongue side) 49 in the same fashion as was shown in FIGS. 2A–2C. However, here, the two jets would be delivered one to the upper set of teeth (e.g., from nozzle 40) and the other jet would be delivered to the user's lower set of teeth (e.g., from nozzle 42). These jets could thus be delivered substantially simultaneously (or alternatively, non-simultaneously, e.g., by cross connections of the inlet lines so that line 44a feeds one set of nozzles and the other line 45a feeds a discrete set such as both of the bottom sets 42, 43).

Then when the other tube, e.g., tube 37, receives a pulse of water from the pump 32 of module 22, it may be delivered up to the handle 25 where the jet first travels through tube 45a, and then may be split into the other two water tubes 45, 47, to feed the other two water jet nozzles 41, 43 via arms 29, 29a. These jets can then spray water from a first side, e.g., the inside (tongue side) 49 toward the other side, e.g., the outside (cheek side) 48, also as shown in FIGS. 2A–2C. Here also, the jets may be substantially simultaneously jetted from nozzles 41, 43 to the respective upper and lower sets of teeth, the jet from nozzle 41 to the upper teeth, e.g., and the jet from the nozzle 43 to the lower teeth.

In one alternative, either a combination of nozzles 40, 42 or a combination of nozzles 41, 43 could be used independently of the other set of nozzles to provide controlled jet action for top and bottom teeth but on only one side (inside or outside) at a time (with alternation available from the first side to the other side as desired). As above, such a singular side usage can provide a singular stream or jet action of water from a singular pump through a singular feed tube, e.g., tube 36, or as above, the two tubes 44a, 45a can be merged into one tube (not shown) which can then feed one set of arms, e.g., arms 28, 28a and thence one set of nozzles, e.g., nozzles 40, 42, and thereby provide an alternating jet action (first from one tube 36, and then from the other tube 37) to and through one set of nozzles. Thus, an effective embodiment using only one side set of nozzles is available. Similarly, a single or the two peristaltic pumps could also feed through one or two feed conduits either a substantially continuous stream or pulsating jets to a single nozzle (or multiple nozzles).

One further alternative to mention which may be used with any of the herein-described alternative embodiments includes a guide member or bite block 60 which is shown in FIG. 2D and which may be positioned on or adjacent any nozzle arm, such as the nozzle arm 28 shown in FIG. 2D (or any of the nozzle arms shown or described herein). The guide member or bite block 60 may used to position the respective nozzle arm or arms in a preferred pre-selected position relative to the teeth and gums so that the resulting jets are appropriately and/or most efficiently directed at the area of most preferred use, e.g., at or adjacent a gum line intersection of the tooth and gum. The guide member or bite block may take many forms, and may be attached to a nozzle arm or may be discrete therefrom. Singular bite blocks or guide members may be used for one or more nozzles, and/or these guide members or bite blocks may be disposed to rest on the crowns of the teeth (as suggested by the guide member 60 in FIG. 2D), or they may curve about and/or encase the tooth or teeth (not shown). Furthermore, they may be relatively stationary in use, or rather move from tooth to tooth with the corresponding nozzle or nozzles during ordinary operation.

Figure 4:
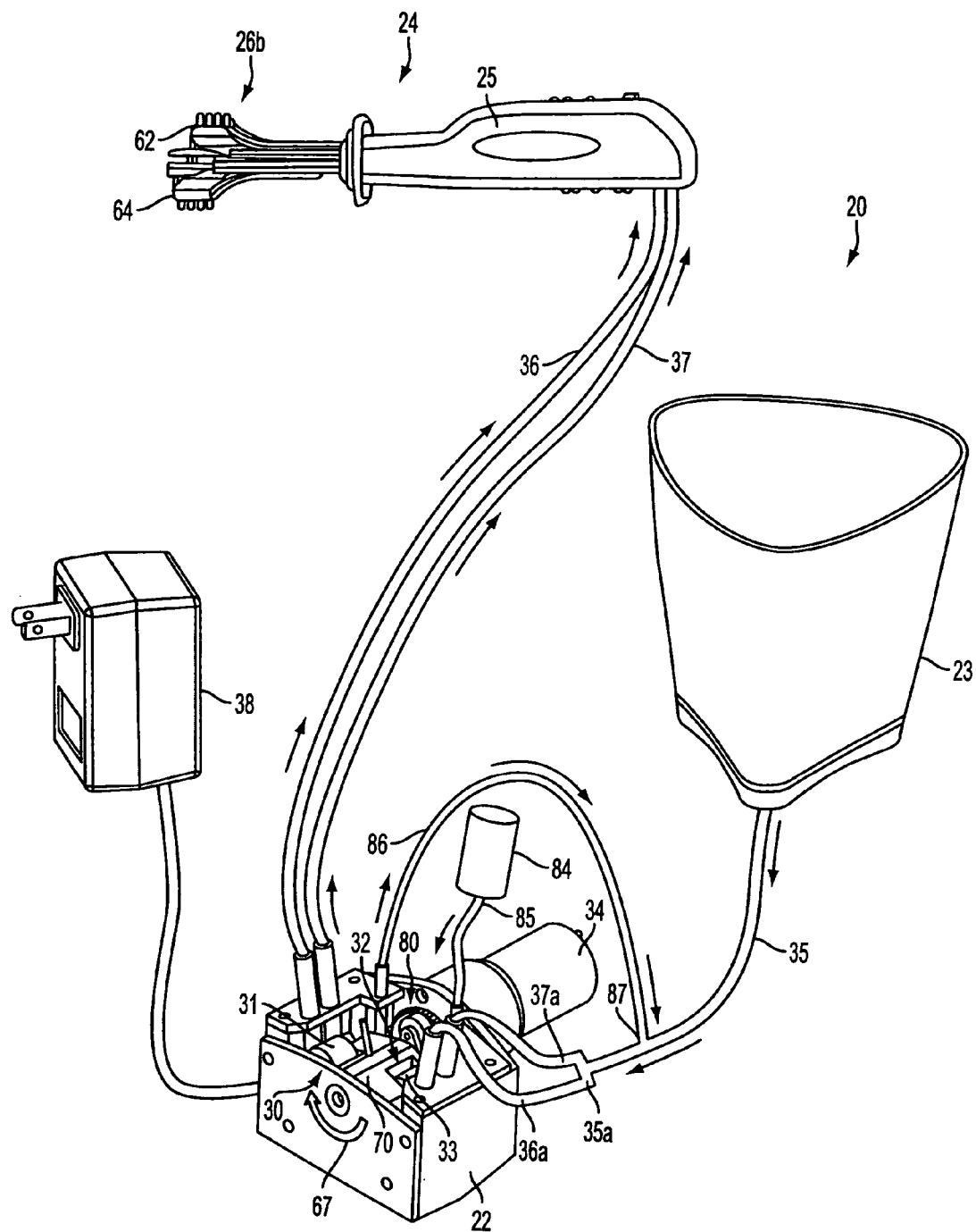
FIG. 4 is an isometric view of yet another alternative oral hygiene device also according to the present invention.
Figure 5:
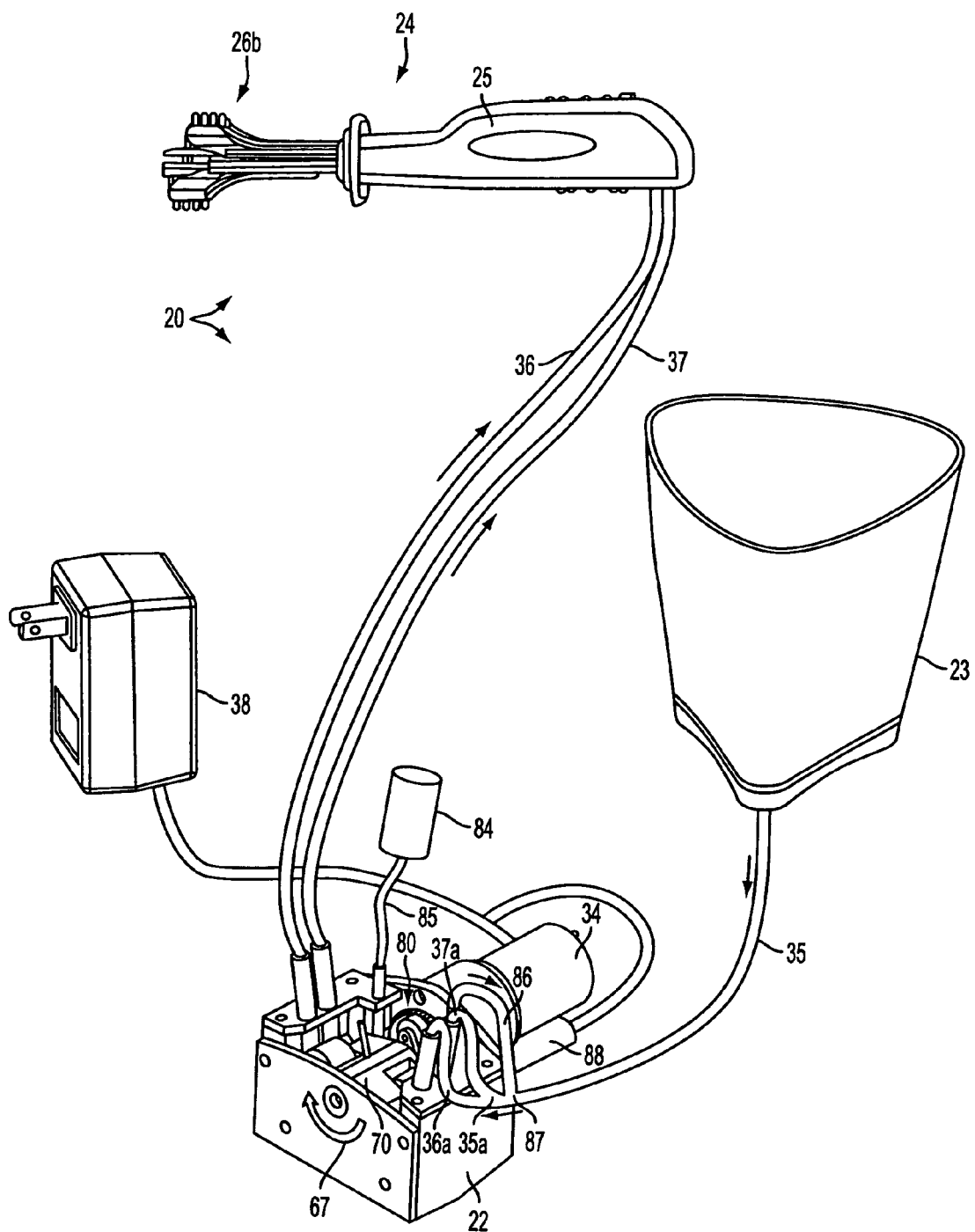
FIG. 5 is an isometric view of still one further alternative oral hygiene device like that in FIG. 4 also according to the present invention.

In a further alternative embodiment, see FIGS. 4 and 5, the irrigation unit 24 has an alternative irrigation sub-assembly 26b which here includes toothbrushes, see e.g., brushes 62, 64. Exemplary brush assemblies for use in alternative embodiments like those shown here may be like those disclosed in co-pending U.S. patent application Ser. No. 60/385,366, filed Jun. 3, 2002, by the same inventor(s) as the present case. The disclosure of that application Ser. No. 60/385,366 is hereby incorporated herein by reference as if fully set forth here. Brushes like these can be used for brushing the teeth substantially simultaneously with the oral irrigation process, but may also be used to position the nozzles in operative position and guide the nozzles throughout the oral cavity for efficient usage. For example, a singular brush head (not directly shown, though could be hidden in the view of FIG. 4) could be used as the guide member like that optional guide member 60 shown in FIG. 2D. Alternatively or in addition thereto, one or more brush heads could be disposed for brushing the sides of the teeth, such as those brushes 62 and/or 64 shown in FIGS. 4 and 5, e.g. Note also that one or more set of brushes could be used with one or two nozzles such as nozzles 40 and/or 41 from FIGS. 1 and 2A–2D, so as to be used with either the top or bottom teeth at one time (alternately usable with the bottom or top teeth at a second or later time), or adjacent nozzles for use with top and bottom teeth at the same time as for example with nozzles 40, and 42, and/or 41, and 43 as shown in and/or described relative to FIG. 3.

Also as shown more particularly in FIGS. 4 and 5, the pumping module 22 can be efficiently packaged. In particular, it may be noted that in order to achieve two streams of water that independently pulsate, two pumps, see e.g., pumps 30, 32, may be used. These two pumps may be located within the pump module 22, and they may be timed, in one embodiment substantially "perfectly timed" to each other to ensure accurate alternating pulses of water.

One type of pump for this application of providing one or more water jets for oral use may be a peristaltic pump. Peristaltic pumps have also been known in various fields of art, however, the use of peristaltic pumps in oral irrigation devices has apparently heretofore been unknown. Peristaltic pumps operate under the principle that a roller pinches or obstructs a flexible tube filled with fluid and then rolls the pinch or obstruction along the tube to thereby drive fluid through the tube. Commonly, peristaltic pumps are of rotational types. Thus, basically in a peristaltic pump, such as either of pumps 30, 32, see FIG. 1 for a more schematic view; a respective single flexible tube, see e.g., tube 36 and particularly the portion 36b disposed in the pump in FIG. 1, may be contained in such a manner that when a roller, see e.g., roller 31, is in rotational contact with the contained tube, e.g., tube portion 36b, the roller squeezes the tube, and in doing so, any liquid caught within the tube in front of or downstream of the roller may be pushed forward by the roller when the roller is moved in a rotational path, as for example along the curvature of the raceway 66 (depicted schematically in FIG. 1) in the direction indicated by the arrow 67 (also in FIG. 1). The fluid within the tube is then moved or pumped inside and along the tube, here e.g., tube 36 until the fluid is delivered to its destination, here e.g., to and through the nozzle 40, e.g.

Figure 6:
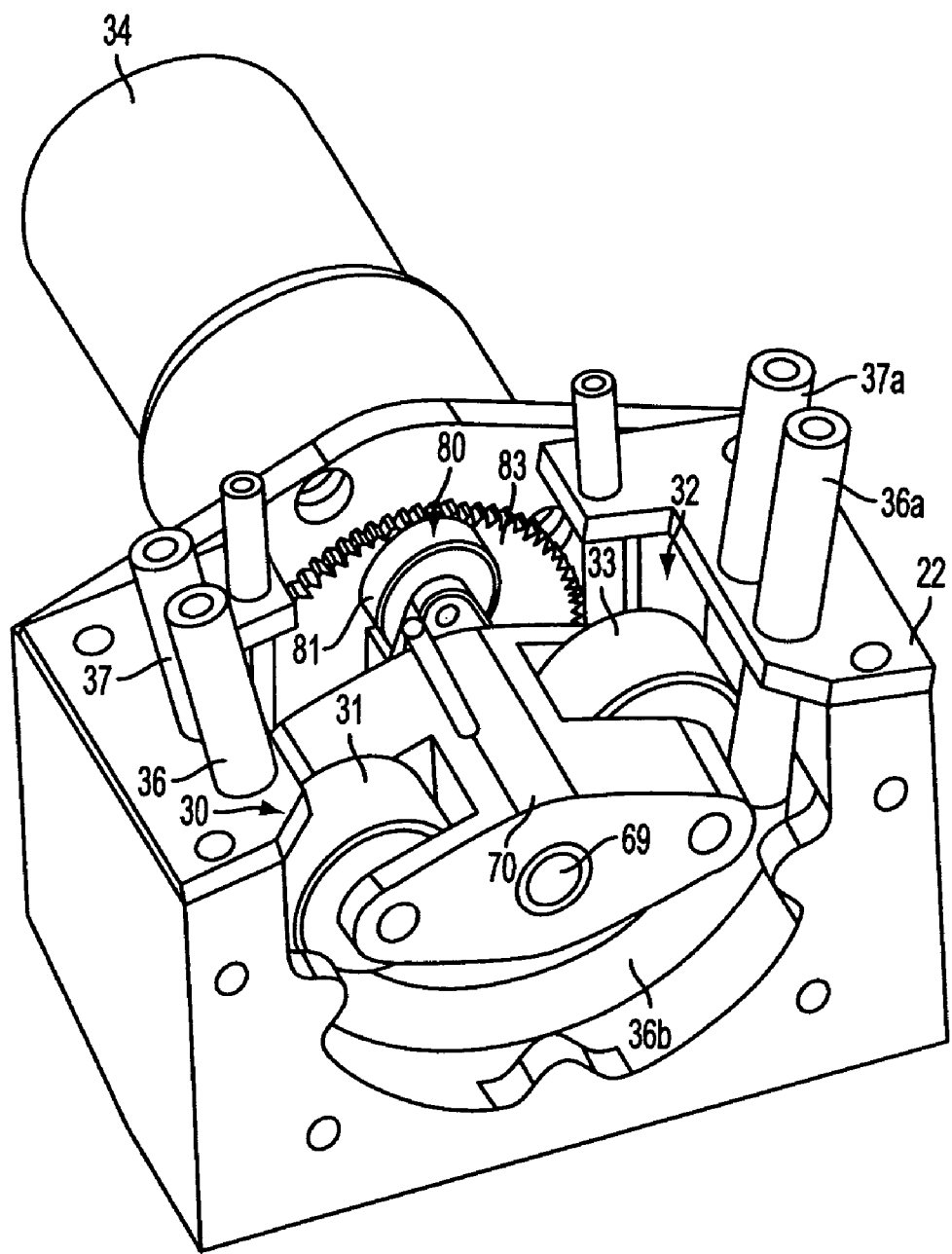
FIG. 6 is an enlarged isometric view of the pump module of the oral hygiene device of FIGS. 4 and 5.

These types of pumps have been known in the art for some time. Even so, an embodiment of the present invention is to "stack" the two water pumps 30, 32 on a common drive shaft, see shaft or axle 69 in FIGS. 1 and 6, in such a manner as to get the automatic pulse action and get it all done in a relatively small package. The axle could be stationary, or could be rotated to thereby rotate the pump arms or rotors and thereby move the rollers in revolution thereabout. Also, the pump stacking may be such that there are separate rotors on or about the axle 69 which could be moved separately though contiguously about the single axle, or as shown by the embodiments of FIGS. 4, 5 and 6, a single rotor 70 could be used which includes all of the pump rollers thereon. Thus, by turning a single rotor 70, all of the pumps associated therewith will also be put in motion, and the rollers thereof put into operative contact with their respective tubes. By stacking the pumps, this assures a sort of perfect pulse "timing" since the two pumps run on a common shaft and are powered by a common motor. In the present incarnation, each pump in the "stack" may have a single roller, see e.g., rollers 31, 33 in FIGS. 1, 4, 5, and 6. The rollers of the two pumps may as shown here be positioned 180 degrees in relation to each other. When the motor shaft 69 makes one-half of a revolution, the first pump 30 delivers one pulse of water to the first one of the delivery tubes, tube 36. When the motor 34 completes the other one-half revolution, such that roller 33 rolls through contact with its tube, the other pump 32 then delivers a pulse of water to outlet conduit 37. This is how the pulses may be "timed." It may also be understood that the reason the water is delivered in pulses from each pump is that a single roller on the tube of each pump is in contact with the tube only during one-half of a complete revolution since the tube in contained in a half circle, not a complete circle. When the roller in not in contact with the tube, there is a moment of water relaxation (no pressure) and as soon as the roller comes in contact with the tube, there is pressure. Pressure is always a result of resistance. Resistance may be obtained by sizing the water jet nozzles in the brushing head correctly (small enough to create enough resistance to obtain the desired water pressure).

Also desirable is a method of injecting dentifrice, flavor concentrate etc. into the water stream. To do this, a third pump 80 may be used. This dentifrice pump 80 may inject/deliver concentrate at a much lower rate than the water pumps, e.g., pumps 30, 32. It has been found that a favorable ratio may be about 100 to 1, water to concentrate. As shown in the drawings, particularly FIGS. 4, 5 and 6, and FIGS. 7 and 8, the dentifrice pump 80 may include one or more rollers, see e.g., roller 81 in FIG. 6 and rollers 81 and 82 in the embodiment of FIGS. 7 and 8. Pump 80 may operate in substantially the same fashion as the water pumps 30, 32, with the possible exception that the dentifrice pump 80 may have more than one roller (see e.g., FIGS. 7 and 8) so that the stream emanating from pump 80 may be substantially continuous instead of pulsating as may more likely be caused by a single roller pump (e.g., pumps 30, 32).

In one embodiment, the third pump, the dentifrice pump 80 may as shown in FIG. 4 be disposed on the axle 69 and may in one embodiment merely rotate thereabout, but be merely driven by motor 34 by a geared down or gear reduction from the driving speed of the other pumps 30, 32. A potential gear for this purpose may be identified in the drawings, see e.g., gear 83 in FIG. 6. (Note, gear 83 could alternatively represent a driving gear for driving the motors 30, 32.)

In any event, the dentifrice or other liquid to be injected into the main water stream may come from a source 84 and flow therefrom through a tube to the inlet of the pump 80. The roller(s) of pump 80 may then move the fluid in peristaltic fashion as described above to an outlet tube 86 which may then connect with the main inlet tube 35 at a T- or Y- (or like) connection 87. This general outline is the same for both of the embodiments of FIGS. 4 and 5; however, in FIG. 5 the flow through the pump is in the opposite direction from that shown in FIG. 4. To achieve this, one embodiment would include a separate pump motor 88. Pump motor 88 can then provide separate power to turn the pump rotor of pump 80 in the opposite direction of pumps 30, 32 even though the pump rotor of pump 80 may be disposed on the same axle 69. This can provide a relatively simple access of the dentifrice outlet tube 86 to the inlet line 35 as shown in FIG. 5.

Figure 7:
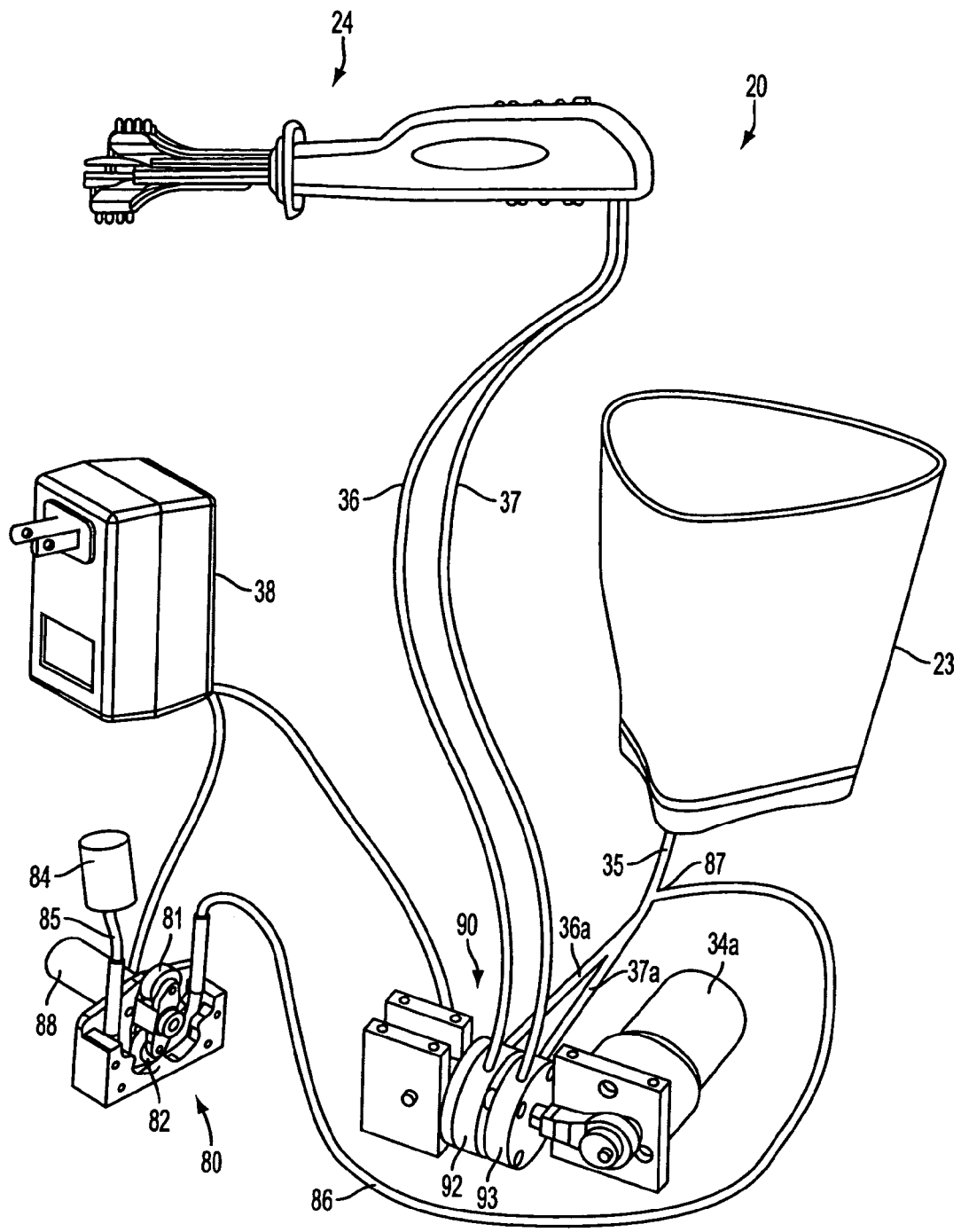
FIG. 7 is an isometric view of yet another alternative oral hygiene device also according to the present invention.

In still further embodiments, alternative pumping arrangements can be used. As shown in FIG. 7 for example, an injection pump 90 may also be used herein. As shown, the injection pump may be fed from a main inlet tubing line 35 from a fluid source 23 as above, and also as before, this main line 35 can be split into two portions 36a, 37a to feed two discrete chambers 92, 93 of the injection pump 90. As further described below, these chambers 92, 93 can then individually and alternately feed the separate feed conduits 36, 37 with streams or pulses of water which can then be used by and fed through the oral irrigation unit 24 in a fashion like that described above for FIGS. 1–6. Check valves (not shown in FIG. 7) like those known in the art may be used to control the flow of water into and out of the respective chambers 92, 93.

Figure 8:
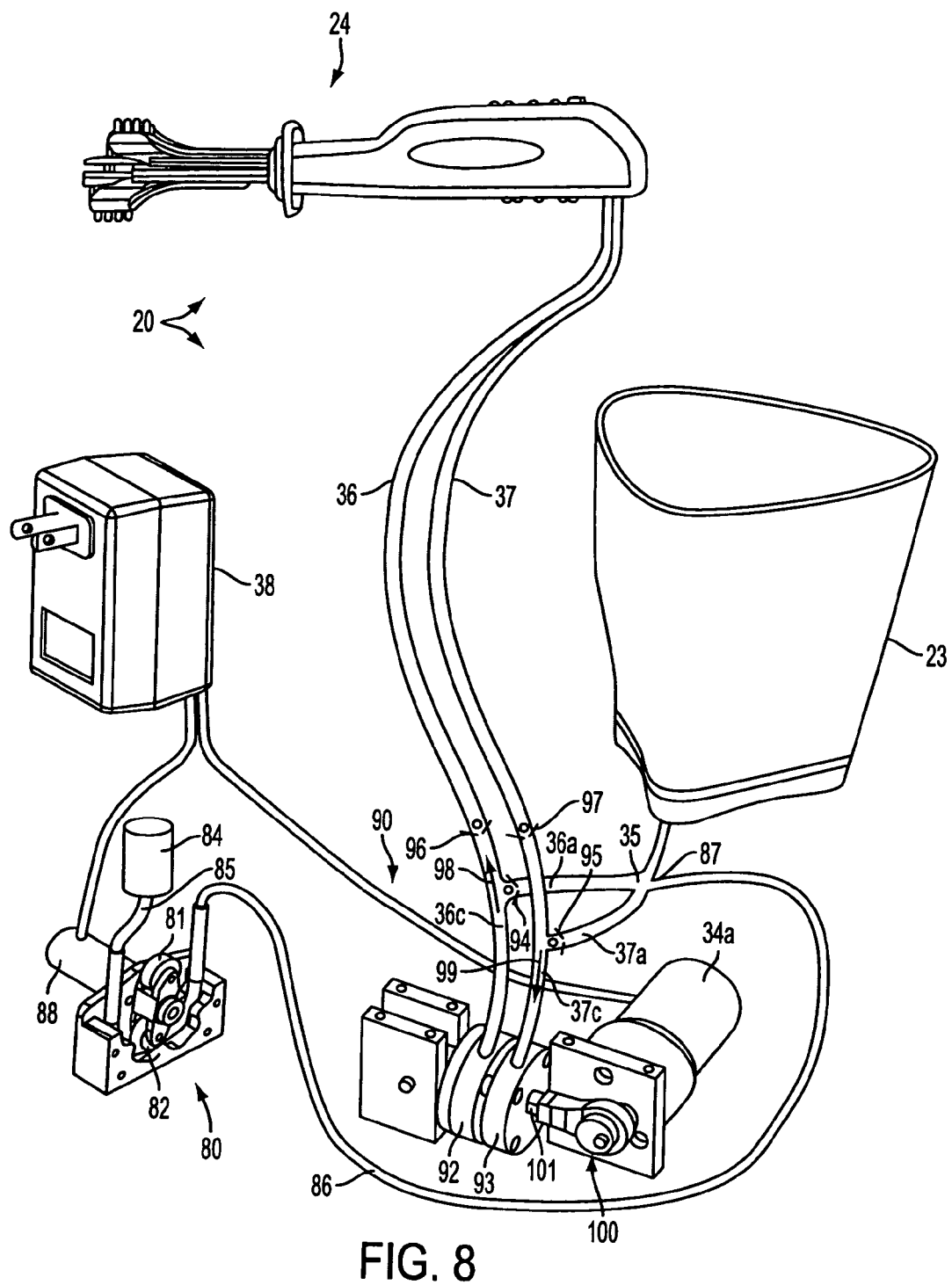
FIG. 8 is an isometric view of an alternative oral hygiene device like that in FIG. 7 also according to the present invention.

Alternatively, an arrangement of check valves (not unlike those which could be used with the embodiment of FIG. 7) may look as shown schematically in FIG. 8. More particularly, a set of inlet check valves 94, 95 may be used to alternately allow flow from respective inlet lines 36a, 37a into the injection pump tubing portions 36c and 37c, and restrict backflow therefrom. Thus, when either chamber 92 or 93 is in the process of providing negative pressure to suck fluid therein from line 35 and source 23, then that suction force will pull open the respective check valve in the respective tubing portion 36a, 37a (see e.g., check valve 95 in line 37a which is shown with an open circle to designate an open condition; a flow arrow 99 also shows the respective flow). Since the typical embodiment may include alternating pumping actions from the respective pump chambers 92, 93, the other check valve (here valve 94) should be in the opposite condition at any given time (this is why valve 94 is shown with a closed circle designating the closed condition of valve 94; a flow arrow 98 also demonstrates the corresponding flow). Substantially simultaneously herewith, a second set of check valves 96, 97 in corresponding outlet/feed conduits 36, 37 (and these also will be in opposite orientation, see valve 96 shown open corresponding to a closed valve 94 and flow arrow 98, while valve 97 is shown closed corresponding to an open valve 95 and a flow arrow 99).

Figure 9:
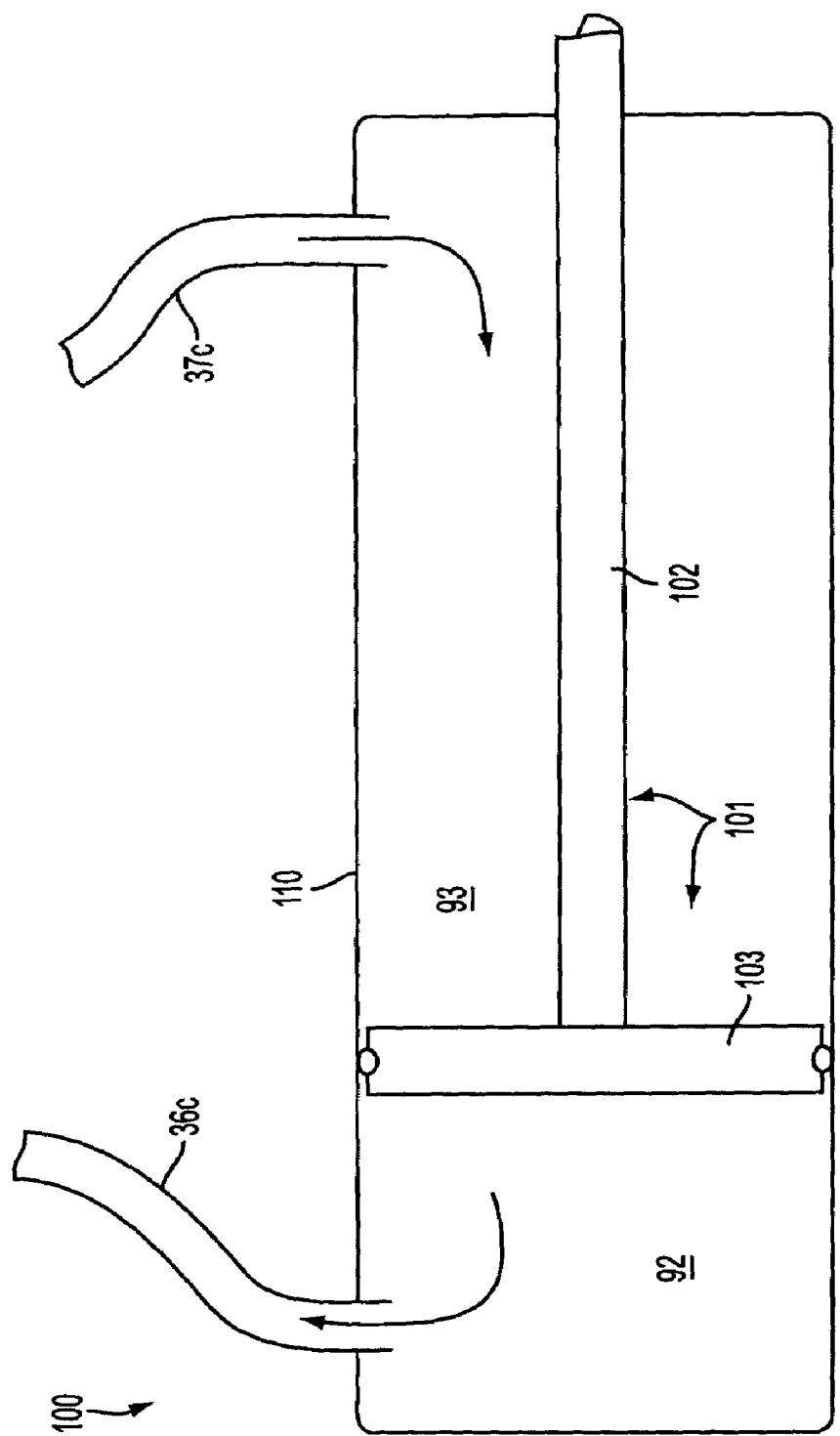
FIG. 9 is a schematic view of a pump alternative which may be used with the oral hygiene devices of FIGS. 7 and 8.

The operation of pump 90 in either of the embodiments of FIG. 7 or 8 may take on the character of a driven piston pump, wherein a piston assembly 100 is driven by a pump motor 34a to drive a piston 101 alternately further in and further out of a piston chamber or chambers. As shown in FIG. 9, this piston 101 can be schematically depicted moving in an overall chamber 110 which includes two sub-chambers 92, 93. Piston 101 can include a rod 102 and head 103 which is movable to move a fluid in and out of each of the respective chambers 92, 93. As shown, the piston is being moved to the left into the sub-chamber 92 to force fluid out through tubing line 36c (which generally matches with the schematic of FIG. 8. At substantially the same time, a suction force is created in sub-chamber 93 by this same movement of piston 101 which draws a fluid into sub-chamber 93 through line 37c (also matching the schematic of FIG. 8). These respective forces cause the opening and closing of the respective check valves 94–97 (in FIG. 8, not shown in FIG. 7) to fill and empty the sub-chambers 92, 93. An alternating jet action of water is thereby delivered to the irrigation assembly 24 and the respective nozzles. Other alternative pumps may also be used here.

Figure 10:
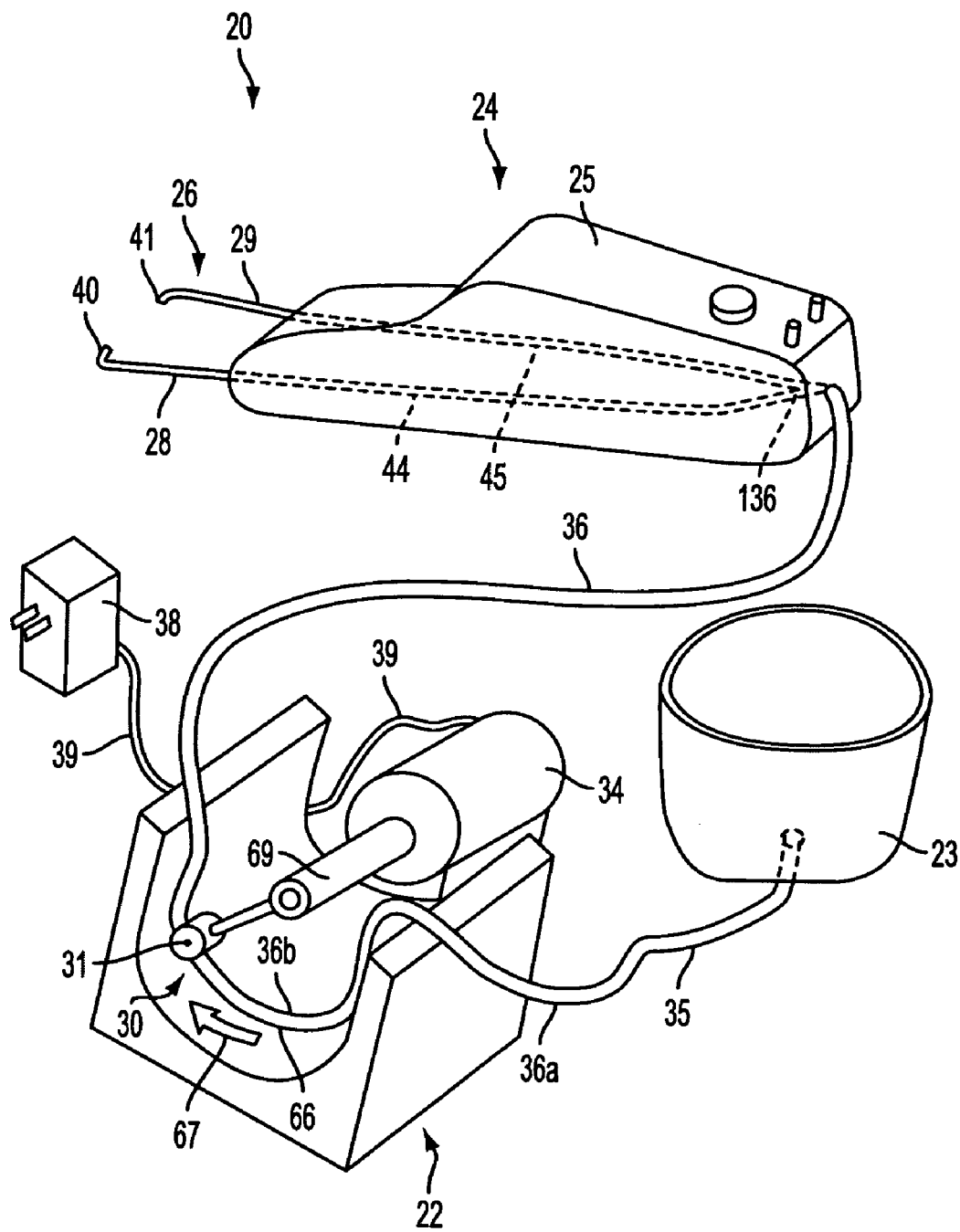
FIG. 10 is an isometric schematic view of an alternative oral hygiene device according to the present invention.
Figure 12A:
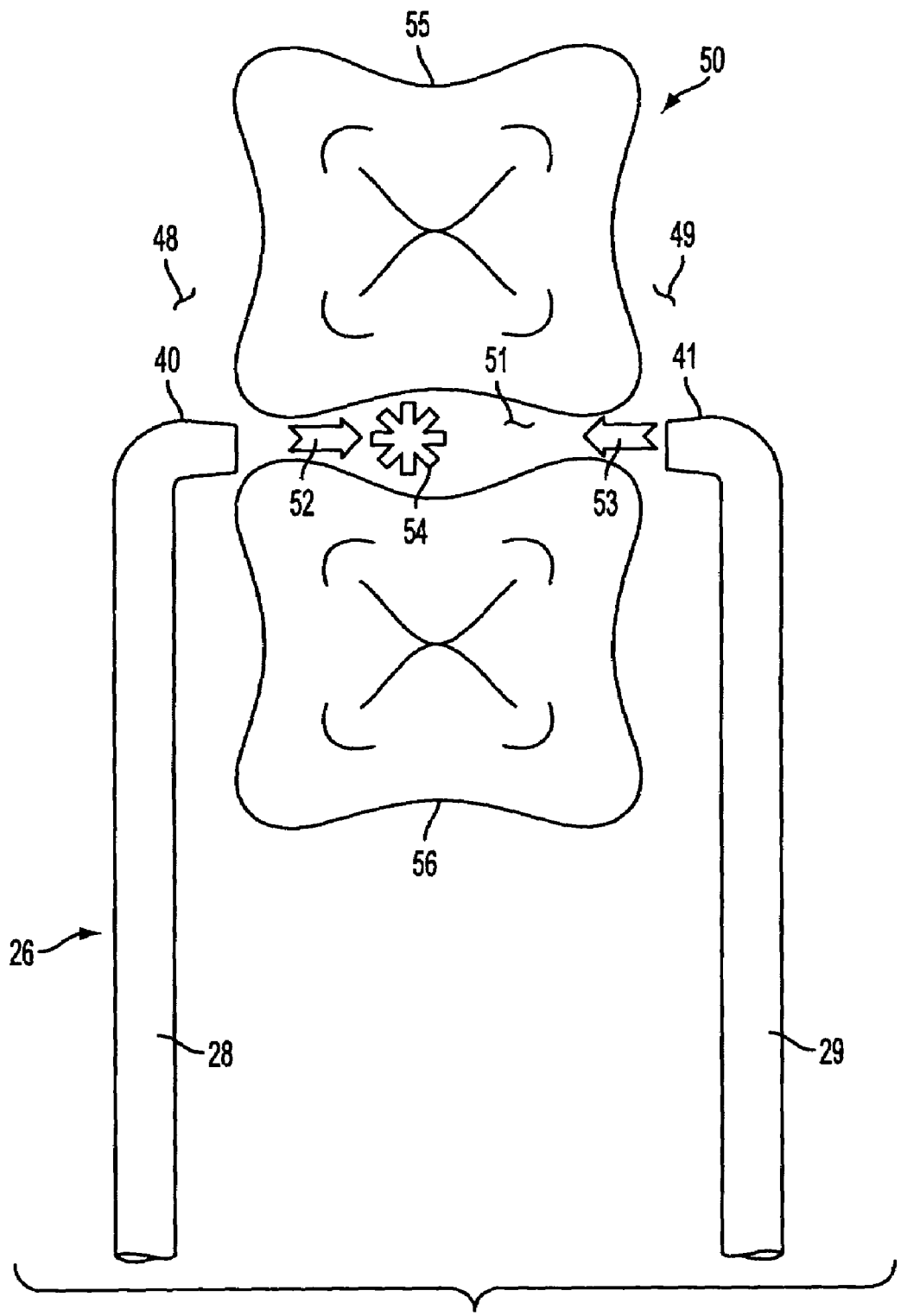
FIG. 12A is a plan view of a cut-away portion of an oral hygiene device of the present invention.
Figure 12B:
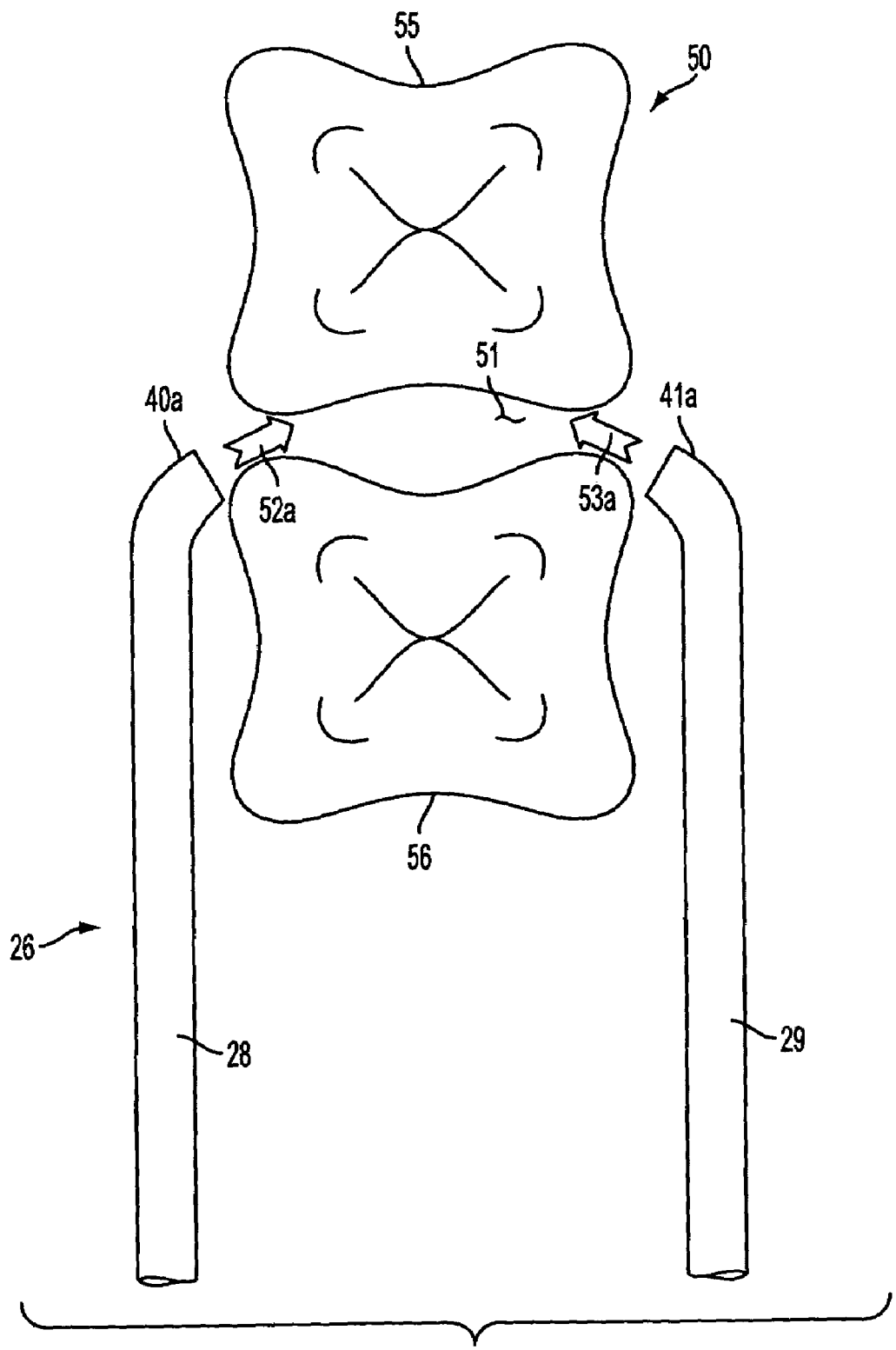
FIG. 12B is a plan view of a cut-away portion of an alternative oral hygiene device of the present invention.

In the next set of embodiments, alternative pumping and/or jetting arrangements will be further explored. For example, in FIG. 10, an alternative embodiment involving only a single conduit 36 from the pump module 22 may be used. Here, a single nozzle 40 could be fed (not shown in singular form in FIG. 10, but see e.g., FIG. 14), or the flow in tube 36 could be split inside the handle 25 of irrigation unit 24 at a Y-split connection 136 into the two lines 44, 45 which lead to the two nozzles 40, 41 via arms 28, 29. In this case, a common line 36 will then feed the two nozzles substantially simultaneously. In the embodiment of FIG. 10, this can involve pulsing jets produced by the single first pump assembly 30 with its single roller 31. As the roller 31 is only engaged part time with the tubing line 36/36b in the pump module, the fluid in the line 36 is allowed a certain amount of relaxation during the non-engaged period such that an alternating relaxation period, then a period of pressure application when the roller 31 then engages the tubing line 36b is experienced by the fluid in the line 36. A pulsating pressure jetting can be the effect. This pulsating jetting may then be provided to and split between the nozzles 40, 41 substantially simultaneously (see e.g., FIGS. 12A and 12B wherein the jets 52 and 53 are shown having left the respective nozzles 40, 41 substantially simultaneously).

Figure 11:
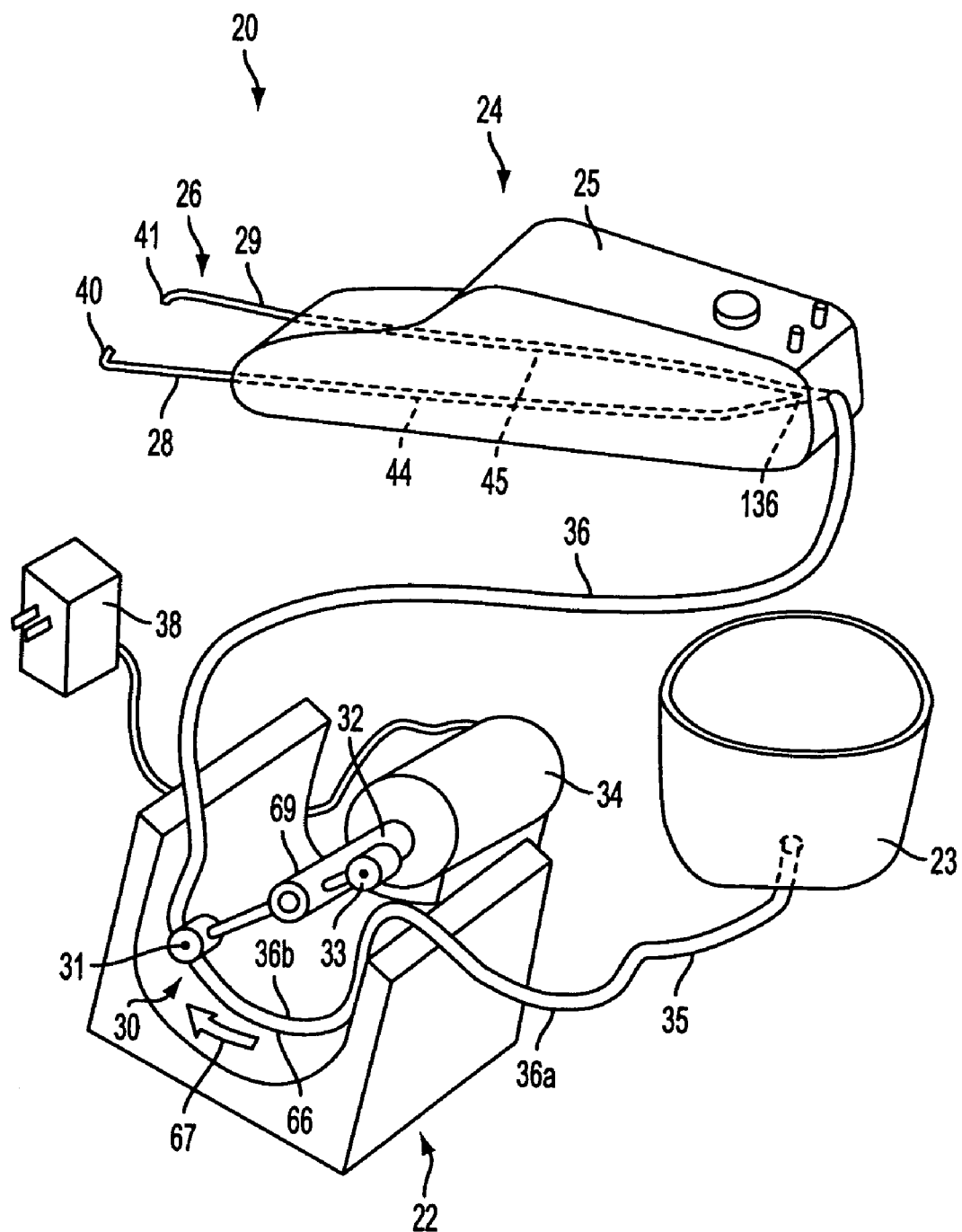
FIG. 11 is an isometric schematic view of yet another oral hygiene device according to the present invention.

In a similar alternative, the pump module 22 shown in FIG. 11 shows a single feed tube 36 split in the handle 25 at a Y-split 136 as in FIG. 10, however, here there are two rollers 31, 33 of two pumping assemblies 30, 32 shown alternately engaging the tube 36/36b in the module. Note, pump assembly 32 has been relatively moved so as to also have its roller 33 be adapted to engage the tube 36/36b. Also, if as suggested here, at least one of these rollers will at substantially all times be in engagement with the tube 36/36a, then no (or little) relaxation will be allowed, and the fluid in the tube 36 will be placed under substantially continuous pressure and a relative non-jetting streaming of the fluid will be caused. These such streams may then be provided to and split between the nozzles 40, 41 (this also can be an interpretation of the schematic of FIGS. 12A and 12B). Peristaltic pumping could be effected with more than two rollers (not shown) to potentially further reduce the pulsatile effect. However, a discrete pulsatile effect could also be generated by two or more rollers when, for example, the tube portion 36b upon which the rollers act, would be disposed in a smaller arc than that shown, or even reduced to a substantially or nearly flat aspect. Thus, numerous or potentially extended relaxation periods could be generated thereby with any of one, two or more rollers.

Figure 13A:
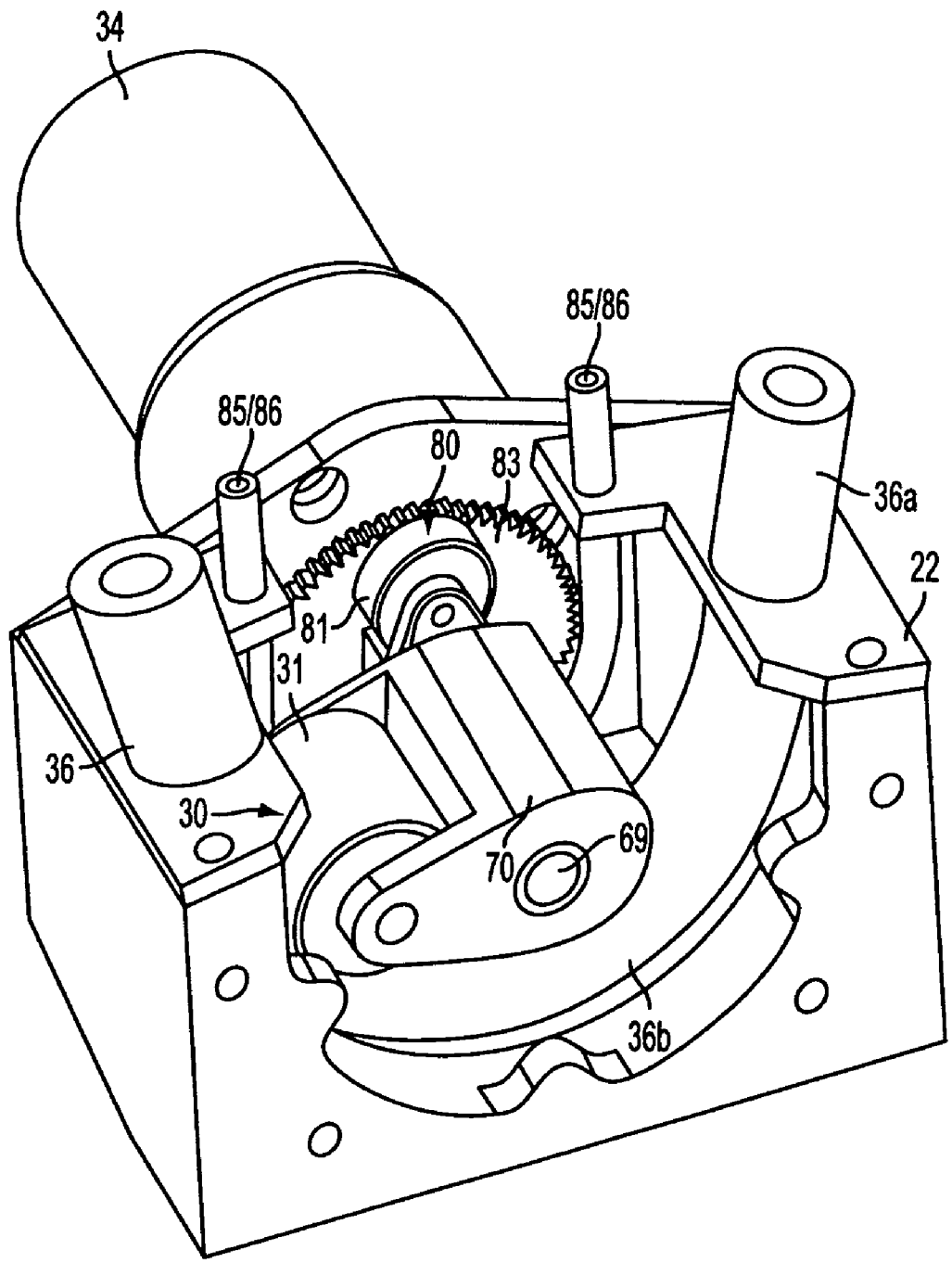
FIG. 13A is an enlarged isometric view of a pump module of an oral hygiene device like that in FIG. 10.
Figure 13B:
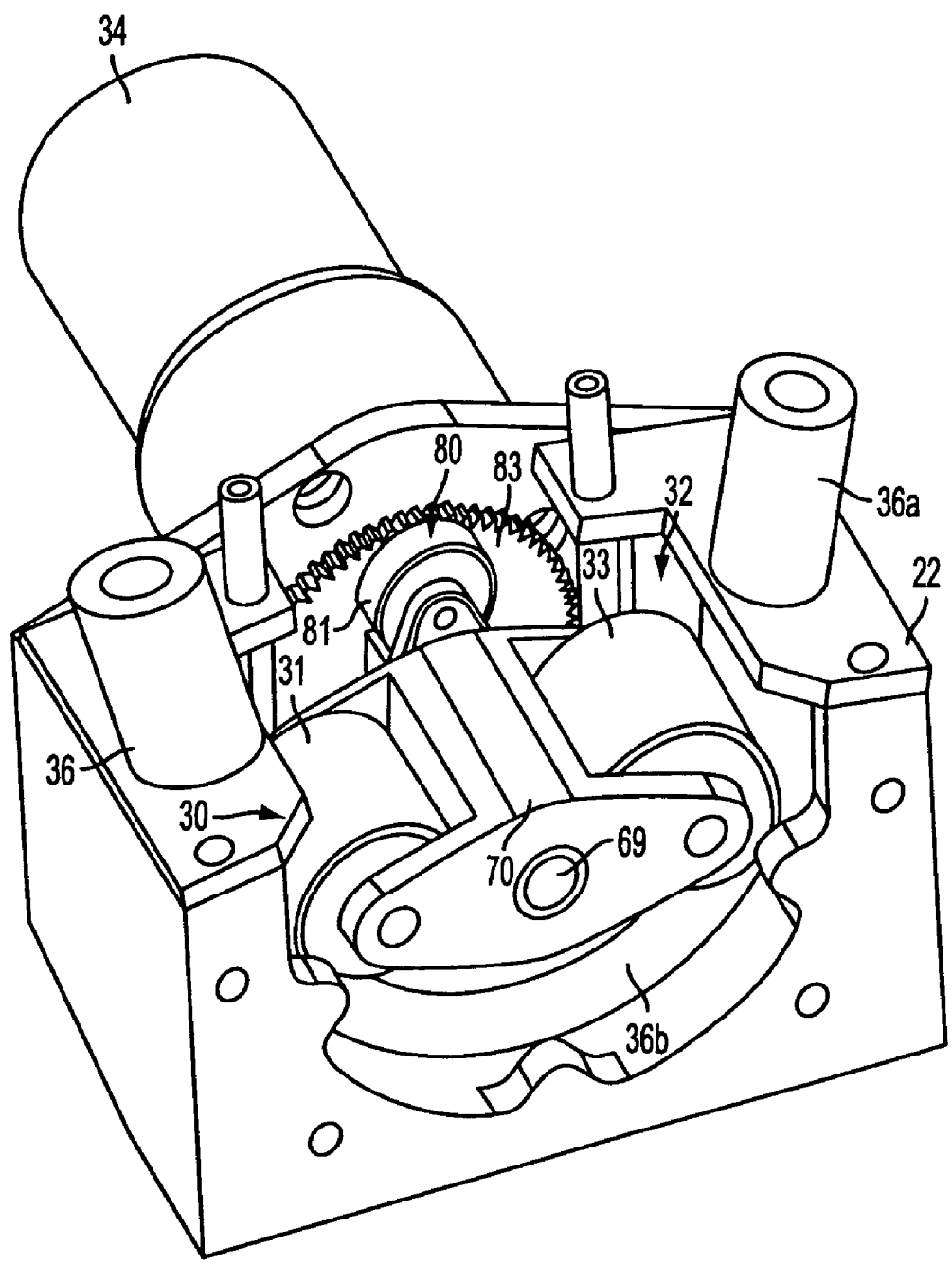
FIG. 13B is an enlarged isometric view of a pump module of an oral hygiene device like that in FIG. 11.

Example pump modules 22 for such embodiments of FIGS. 10 and 11 (though not limited hereto) are shown in more detail in FIGS. 13A and 13B. A single roller 31 embodiment is depicted in FIG. 13A and a dual roller embodiment in FIG. 13B. Thus, pulsing jets would more likely result from use of a single roller pump assembly 30 as in FIG. 13A and more stream-like or streaming would result from the dual pump 30, 32 embodiment of FIG. 13B. Note, a further (second/third/dentifrice) pump 80 is also shown in FIGS. 13A and 13B as such could be used with any of the embodiments herein described. This pump 80 may be like that described in detail above (see FIGS. 6, 7 and 8, e.g.), and will also be addressed in some more detail with respect to FIGS. 14 and 15, below.

Figure 14:
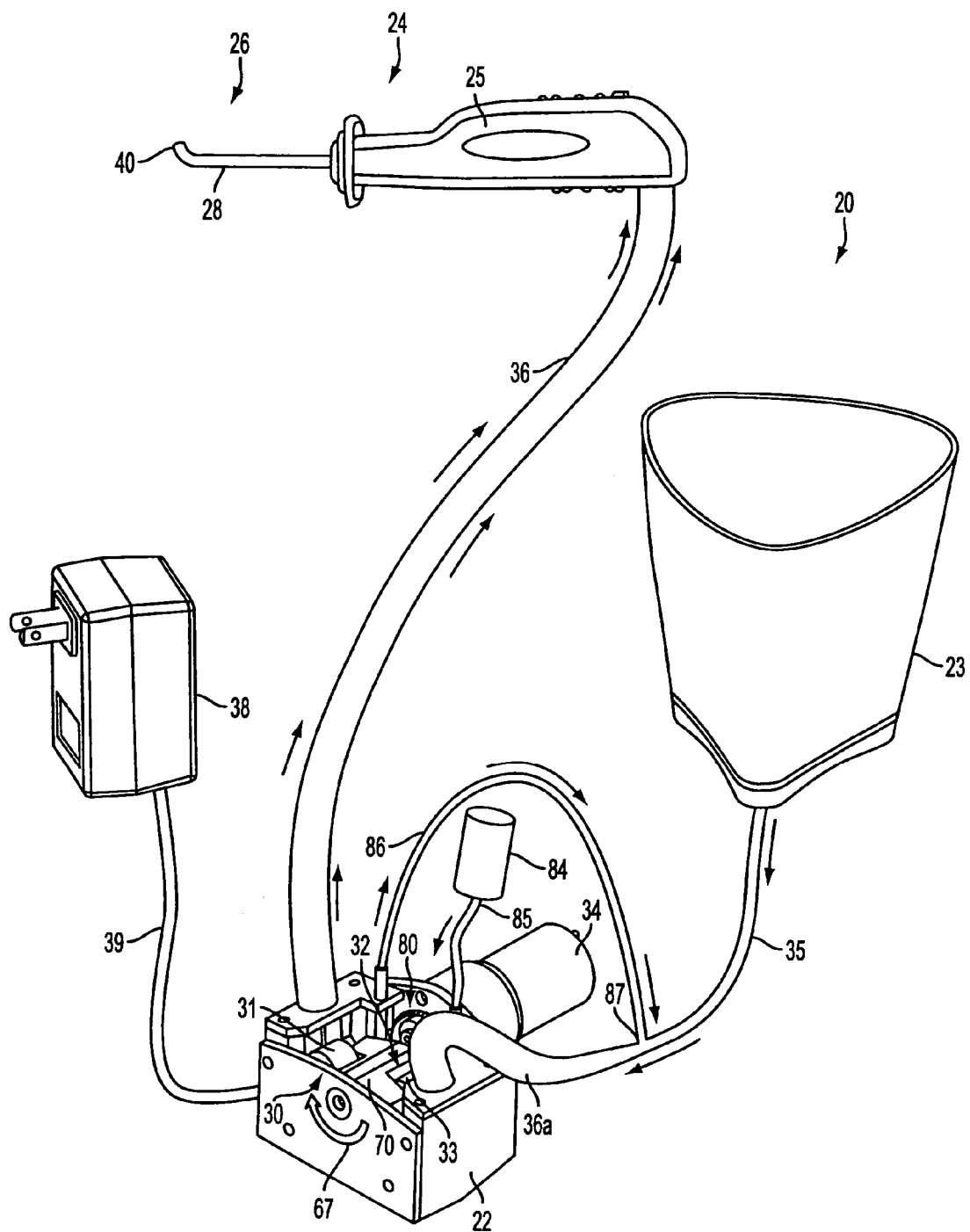
FIG. 14 is an isometric view of yet another alternative oral hygiene device also according to the present invention.
Figure 15:
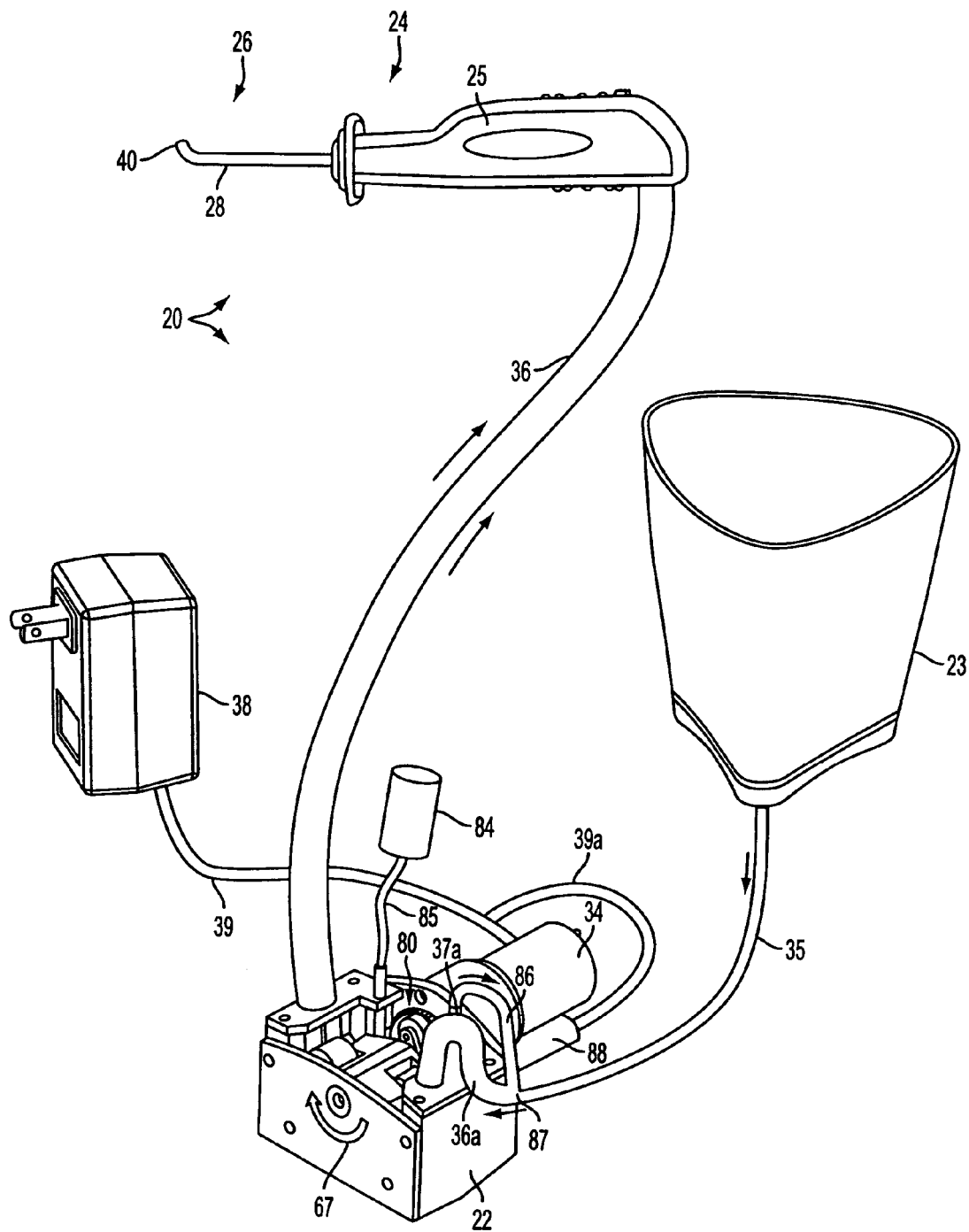
FIG. 15 is an isometric view of still one further alternative oral hygiene device like that in FIG. 14 also according to the present invention.

As shown in FIGS. 14 and 15, a handle 25 having one or more nozzles 40 (only one shown here) may be connected via a tubing line 36 to a pump module 22 having one or more pump rollers (see e.g., FIGS. 13A and 13B). The pump module may then be fed by a feed line 35 fed by a source 23 (as generally described above), such that a fluid disposed in and/or from the source 23 can then be communicated to the pump and thence to the handle and the nozzle(s) (note, one or more splits in or adjacent the handle could be used to feed more nozzles as described herein). If a dentifrice or other fluid is desired to injected into the main line 35, a further pump 80 can be used to take such fluid from a injection container 84, via an inlet line 85 pumped via one or more rollers 81, 82 to and through an outlet line 86 to an injection connection 87 to line 35. As before, this further pump assembly 80 can be run off the main motor 34 (via a gearing arrangement, usually to gear down the speed ratio) as shown by FIG. 14, or it could be run off a second motor 88 (FIG. 15) driving a gear 83 (FIGS. 13A and 13B). In either case, power can be provided to the motor 34 from the power supply 38 via power cord 39 (with the additional branch cord 39a for the second motor 88) which are shown schematically in FIGS. 14 and 15.

Figure 16:
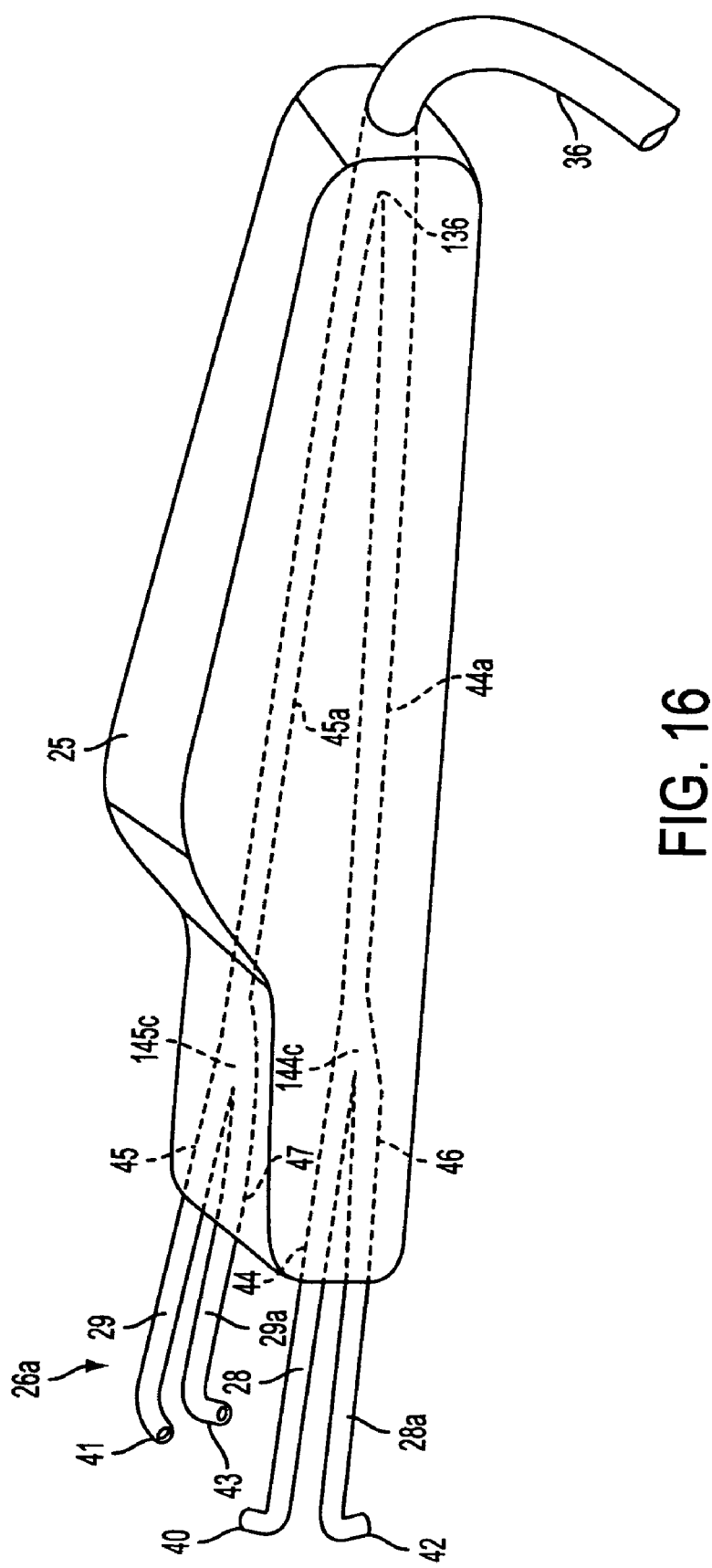
FIG. 16 is an isometric view of an alternative oral hygiene device also embodying the present invention.

Note also that though not shown, an injection pump (see e.g., FIGS. 7, 8 and 9) or other pumping mechanisms (not shown) could also alternatively be used herein for pumping to one or more cleaning nozzles, e.g., nozzles 40 and/or 41 and/or 42 and/or 43. Moreover, one or more branch connections like connection 136 (FIGS. 10, 11 and 16) may be used. For a further example, as shown in FIG. 16, one feed line 36 can be broken into two supply lines 44a, 45a by a branch connection 136, and these supply lines can be further broken down into further supply lines such as lines 44, 46 by connection 144c in line 44a, and/or lines 45, 47 by connection 145c in line 45a. Thus, multiple nozzles can be fed by one (or more) original lines 36 (or the like). Here as above, nozzles 40 and 41 can be used for either sides of the upper teeth while substantially simultaneously, nozzles 42 and 43 can be used for the lower teeth. Note further that any or all of these branching connections 136, 144c, and/or 145c can be as shown, disposed in the handle 25 or they may be disposed outside the handle 25 (not shown) adjacent thereto, or even disparate therefrom, and yet not depart from the principles of the present invention.

In a further set of embodiments, moving shafts for moving cleaning arms/heads will be shown and described. For example, in FIGS. 17 and 18, there is a depiction of an isometric cut-away view of a handle 125 of an irrigation unit 124 which includes mechanisms for moving one or more cleaning arms 128, 129 (two shown here) of an irrigation assembly 126. More particularly, one or more structural shafts 200, 201 may be disposed in reciprocal motive disposition in and relative to the control handle 125. Shafts 200, 201 may, as shown be relatively contiguous with or otherwise connectable to arms 128, 129. One or more nozzles 140, 141 (again, two shown here) can thence be contiguous with arms 128, 129, as shown, or detachably attachable to the ends of the structural shafts/arms 200/128, 201/129. When the nozzle(s) 140, 141 are installed in/on respective shafts 200, 201, the respective water tubes 144, 145 (shown schematically), connect to and/or pass through respective holes or hollow portions of the shafts 200, 201 to communicate fluid therethrough to the respective nozzles 140, 141.

Figure 17:
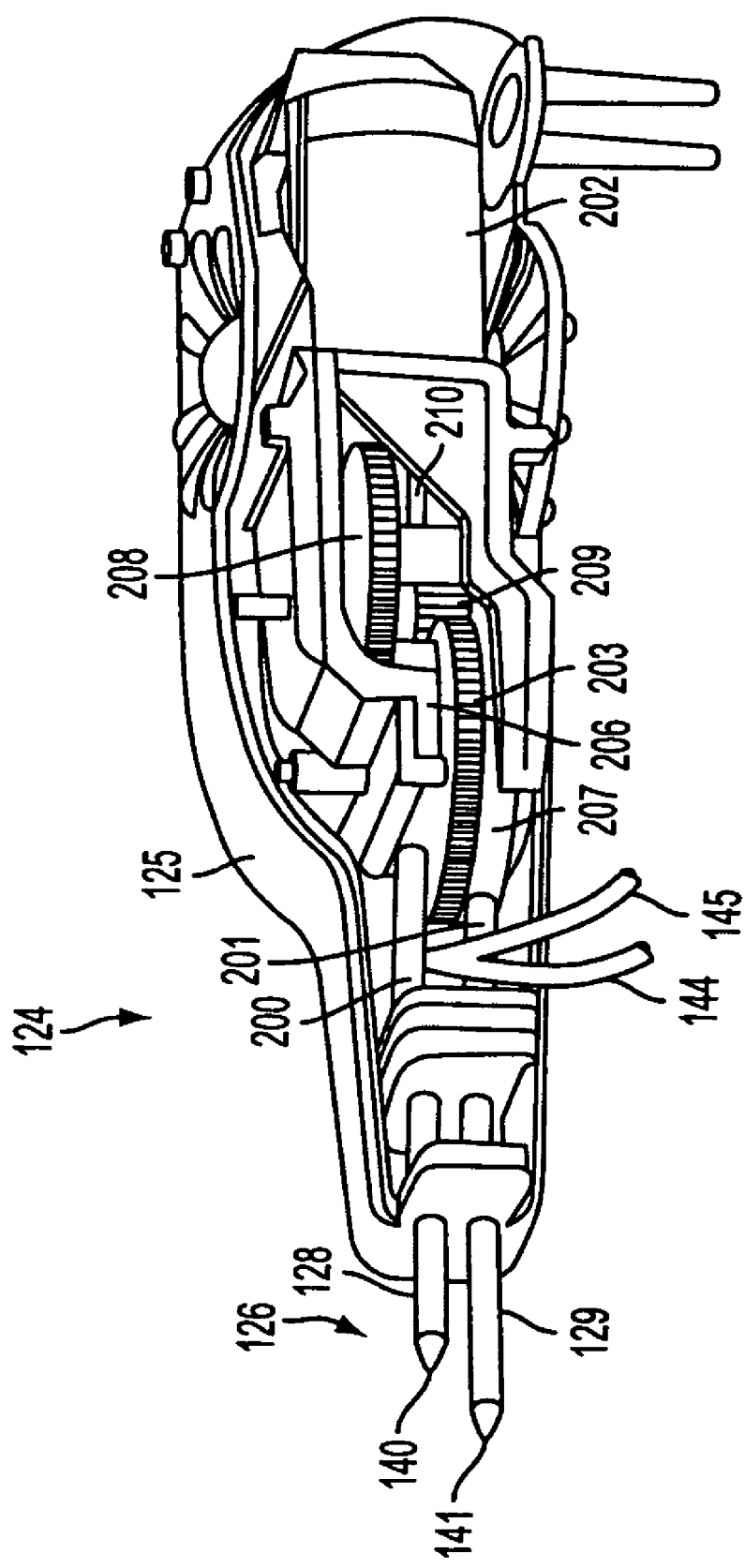
FIG. 17 is a cut-away isometric view of an embodiment of the present invention.
Figure 18:
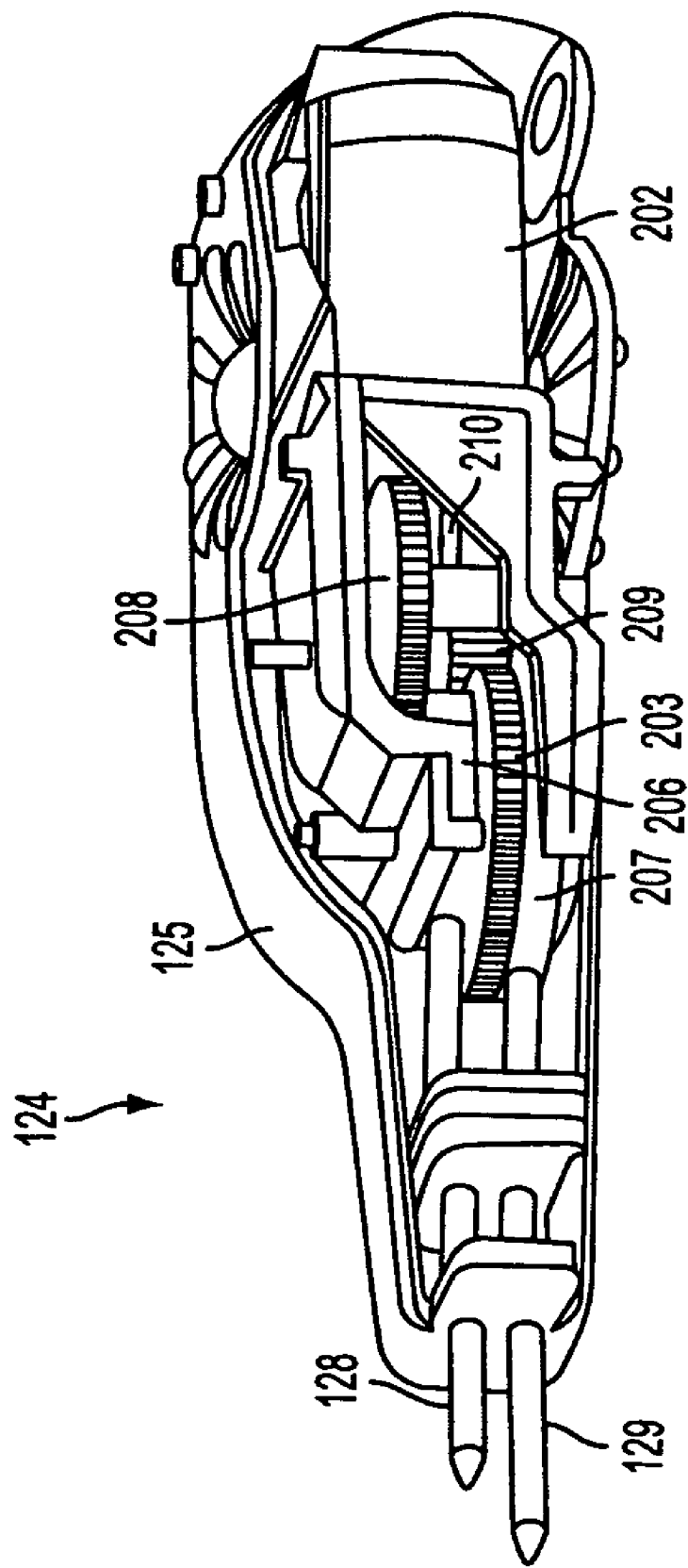
FIG. 18 is a cut-away isometric view of another embodiment of the present invention.
Figure 18A:
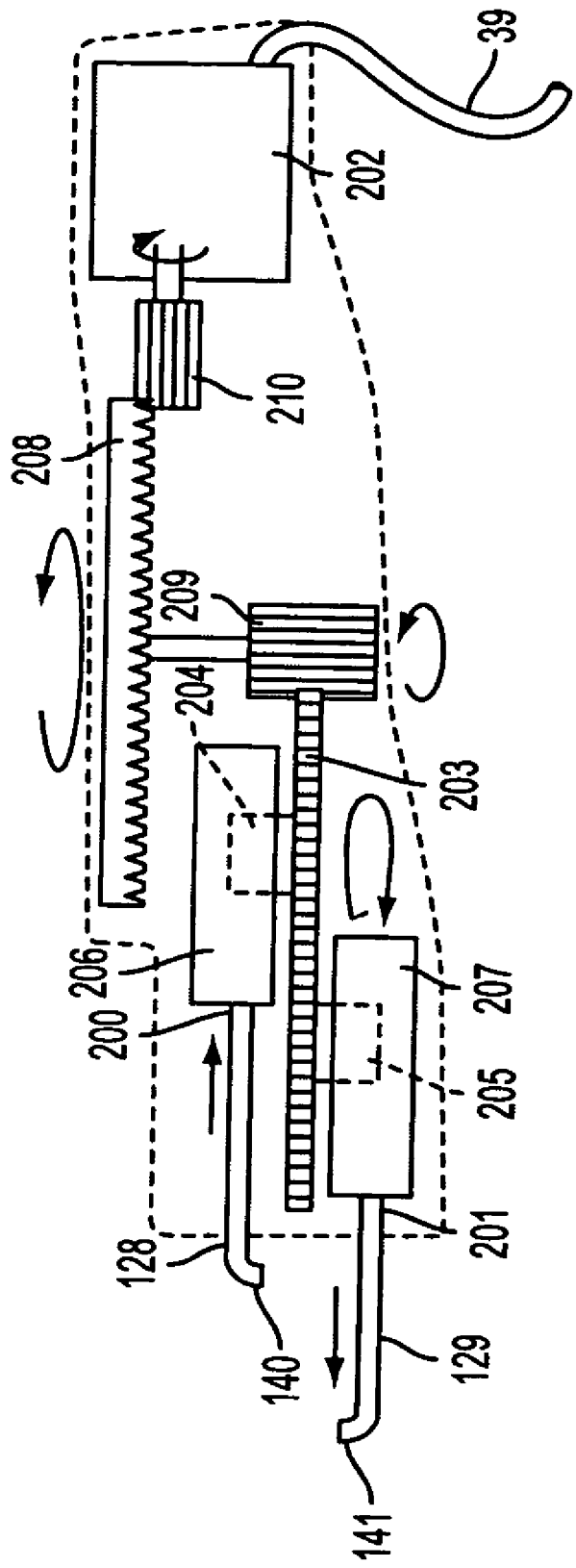
FIG. 18A is an elevational view of some interior components of a device according to an embodiment of the present invention.
Figure 19:
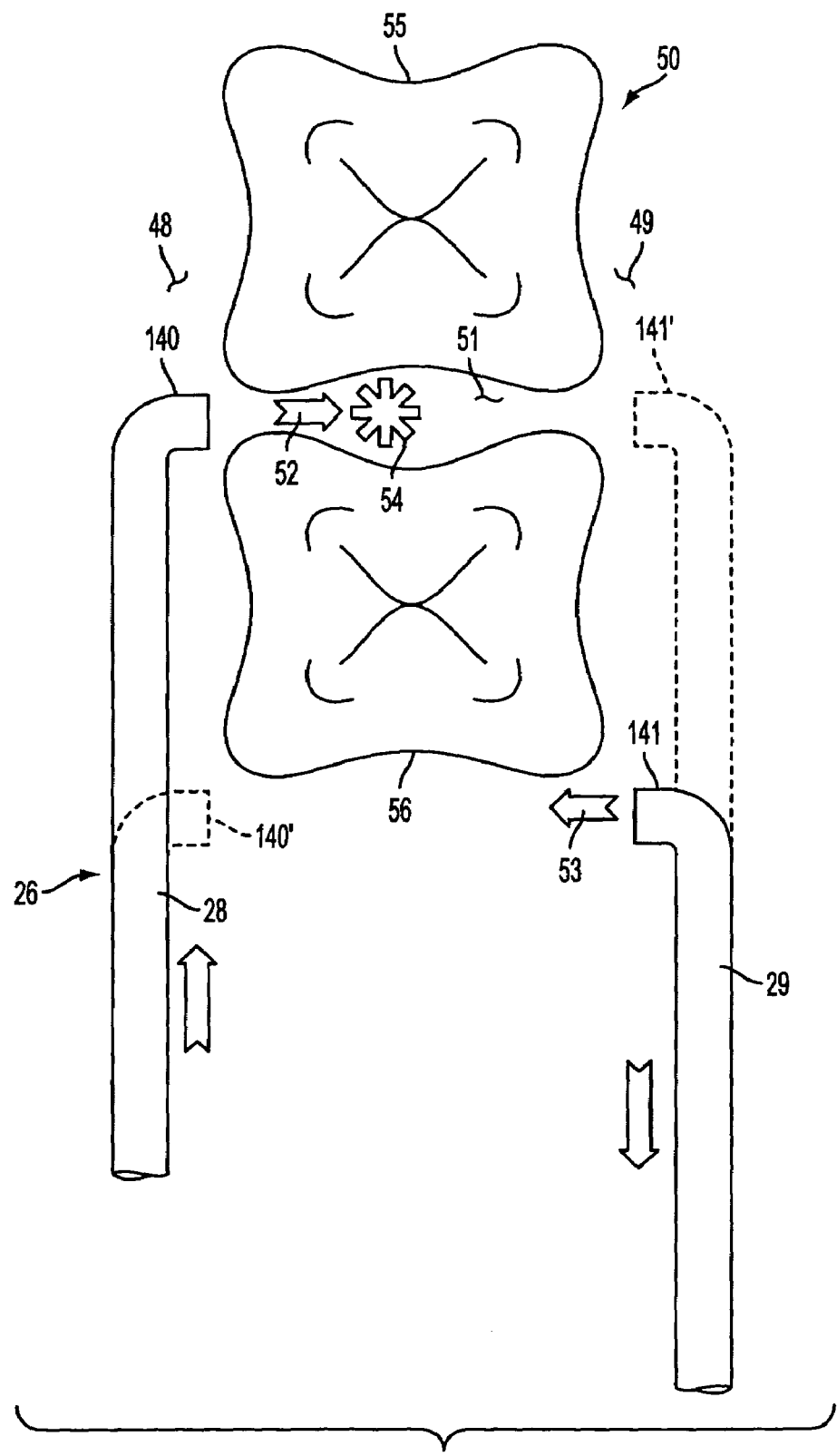
FIG. 19 is a plan view of a cut-away portion of an alternative oral hygiene device of the present invention.

Inside the control handle 125 may be a direct current (DC) motor 202 that may provide primary power to reciprocate the nozzle heads 140, 141. The heart of the double reciprocal/opposing movement described and shown here may be a gear 203 with respective cams 204, 205 one each on opposite sides of the gear 203 (see FIG. 18A). The upper cam 204, the spur gear 203, and lower cam 205 may all be combined as one piece. Structural shafts/arms 200/128 and 201/129 may be attached to cam followers 206, 207 within the power handle 125. As shown in FIGS. 17, 18, and 18A, a system of gears may be used, in some embodiments, to ultimately move the cleaning heads 140, 141. The system may include, as shown, a crown gear 208 connected by a shaft to a reduction spur gear 209 which communicates in gear meshing relationship with the double cam gear 203. A motor gear or pinion may be disposed in operative gear meshing relationship with the crown gear 208. Thus, when the DC motor 202 runs, its pinion gear 210 turns the crown gear 208 which may be attached to small spur gear 209 which in turn may be in contact with the double-cam big spur gear 203 which may thus by contact move the two cam followers 206, 207 to move in and out the arms/nozzles 128/140, 129/141 relative to the power handle 125. Thus, this causes the structural shafts 200, 201 to reciprocate in opposing directions and thereby provide for alternating dispositions of the nozzle heads 140, 141 as shown in FIG. 19, for example, the positions being reversible such that at one moment, the heads are as shown, and then they may be reciprocated such that they switch relative distances inside the mouth. The switched position is shown in FIG. 19 in dashed lines with a relatively lower, more outward nozzle 140' shown relative to the relatively raised, more inward nozzle 141'.

The result is a simplification such that only one inlet tube, e.g., tube 36 may be used to provide a good alternating pulsatile action, alternating in that only one jet pulse will be directed at a piece of debris 54 at a time even though the pulses will be delivered to and leave the nozzles at substantially the same time. Then, the potentially simplest one roller peristaltic pump embodiment (see e.g., FIGS. 10 and 13A) may be used to yet provide alternating pulses. Moreover, the moving jet heads make the pulsing water more active in the user's mouth, particularly when compared to the stationary nozzle embodiments where the user must move the handle to move the jet heads. If the user does not move that embodiment actively, then the jets will be less active relative to the entire mouth area, and the jets could even be substantially stagnant in acting in limited or only in the places that the user specifically directs their use. This can then aid in reducing if not eliminating human error.

Figure 18B:
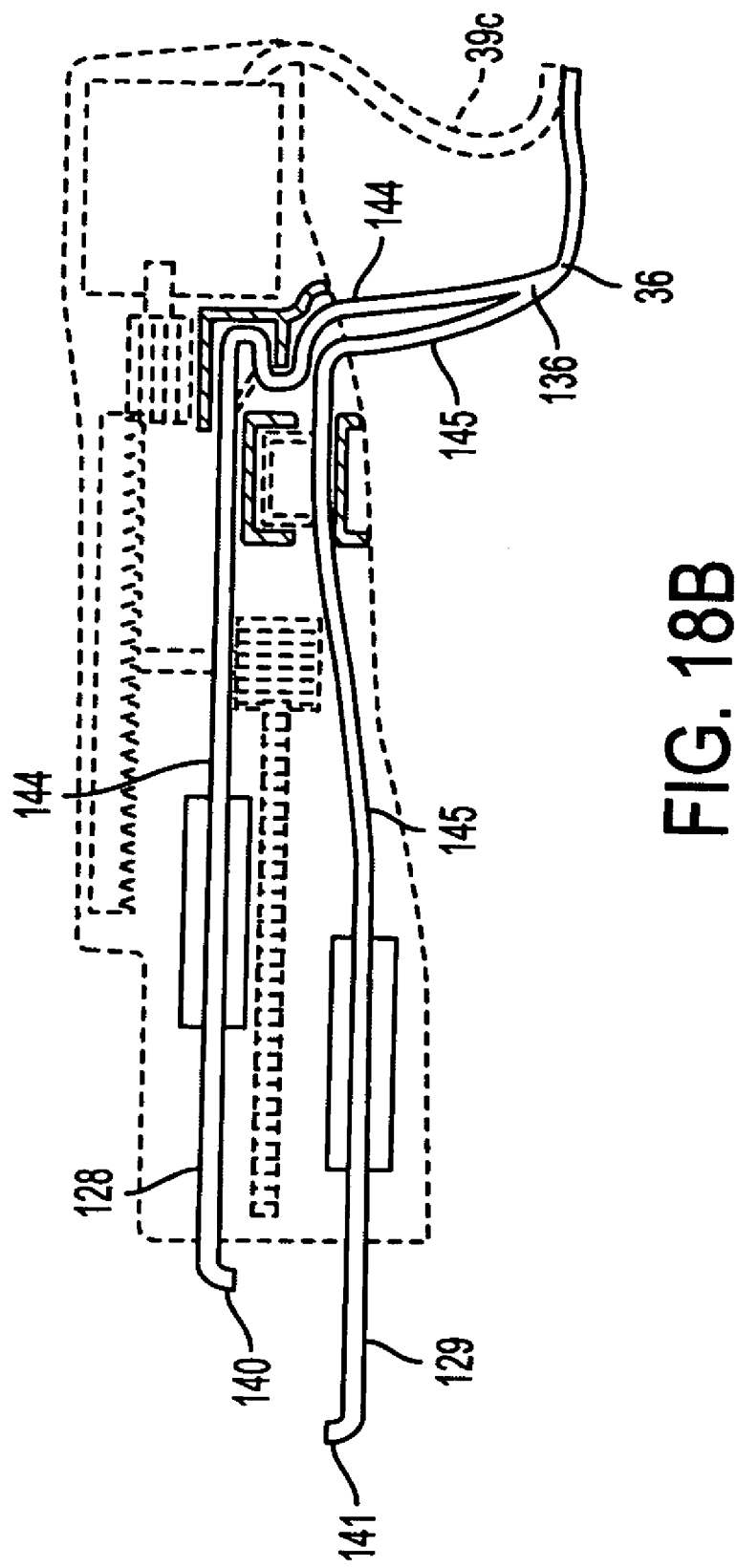
FIG. 18B is an elevational view of some other interior components of a device according to an embodiment of the present invention.

Note, in the tubes/conduits 144, 145 may preferably be relatively flexible or resilient at least in a portion of their location within the handle 125 at or near their respective connection areas 214, 215. Thus, the tubes or hoses 144, 145 may at or in the connection areas 214, 215 be flexibly disposed such that each has enough clearance to allow the nozzle head 140, 141 to reciprocate in and out of the handle 125 and relatively fold into and alternately extend out of their respective areas 214, 215 as shown in FIG. 18B. The respective rolling in and extending out are shown in dashed lines.

Figure 20:
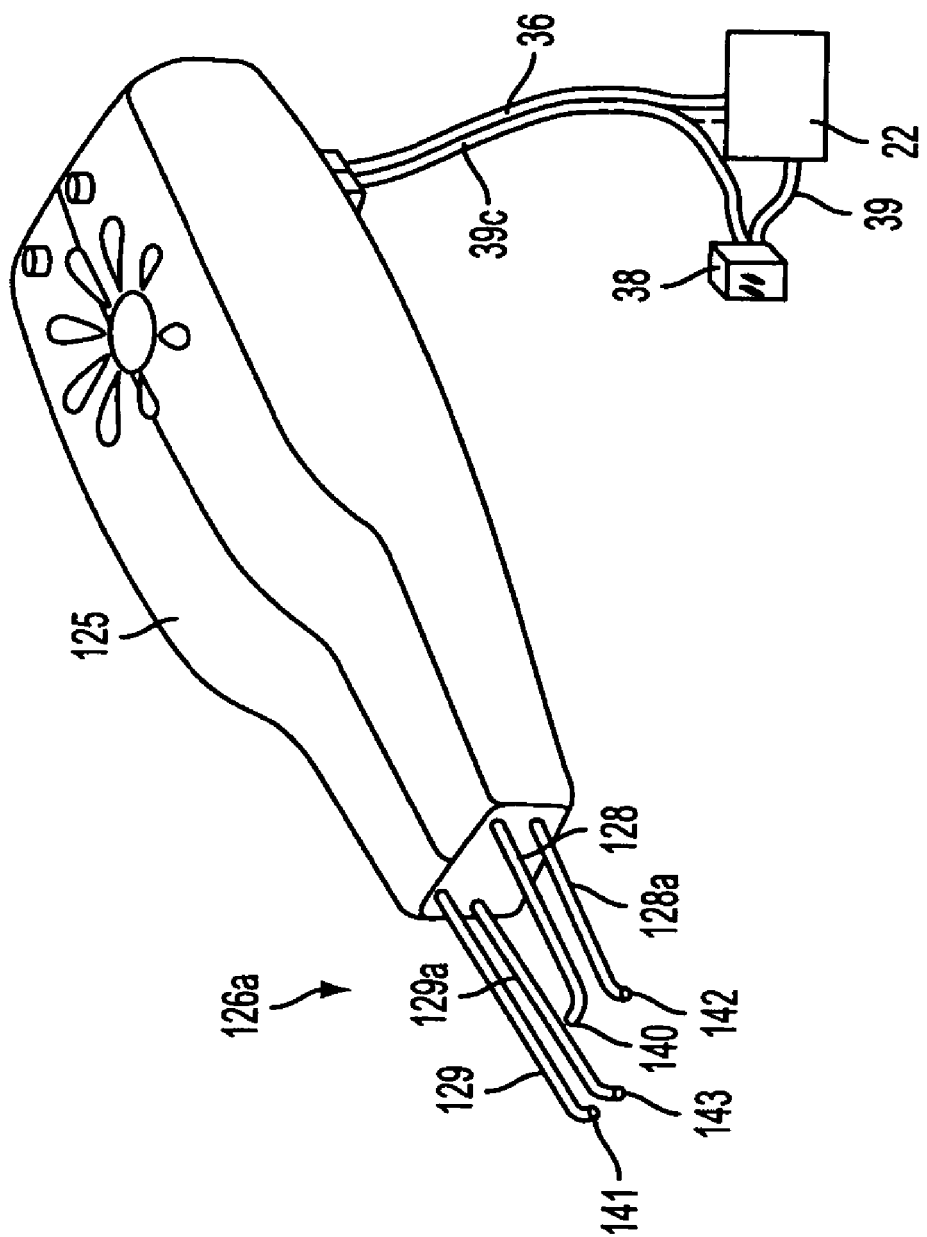
FIG. 20 is an isometric schematic view of yet another alternative oral hygiene device also according to the present invention.
Figure 20A:
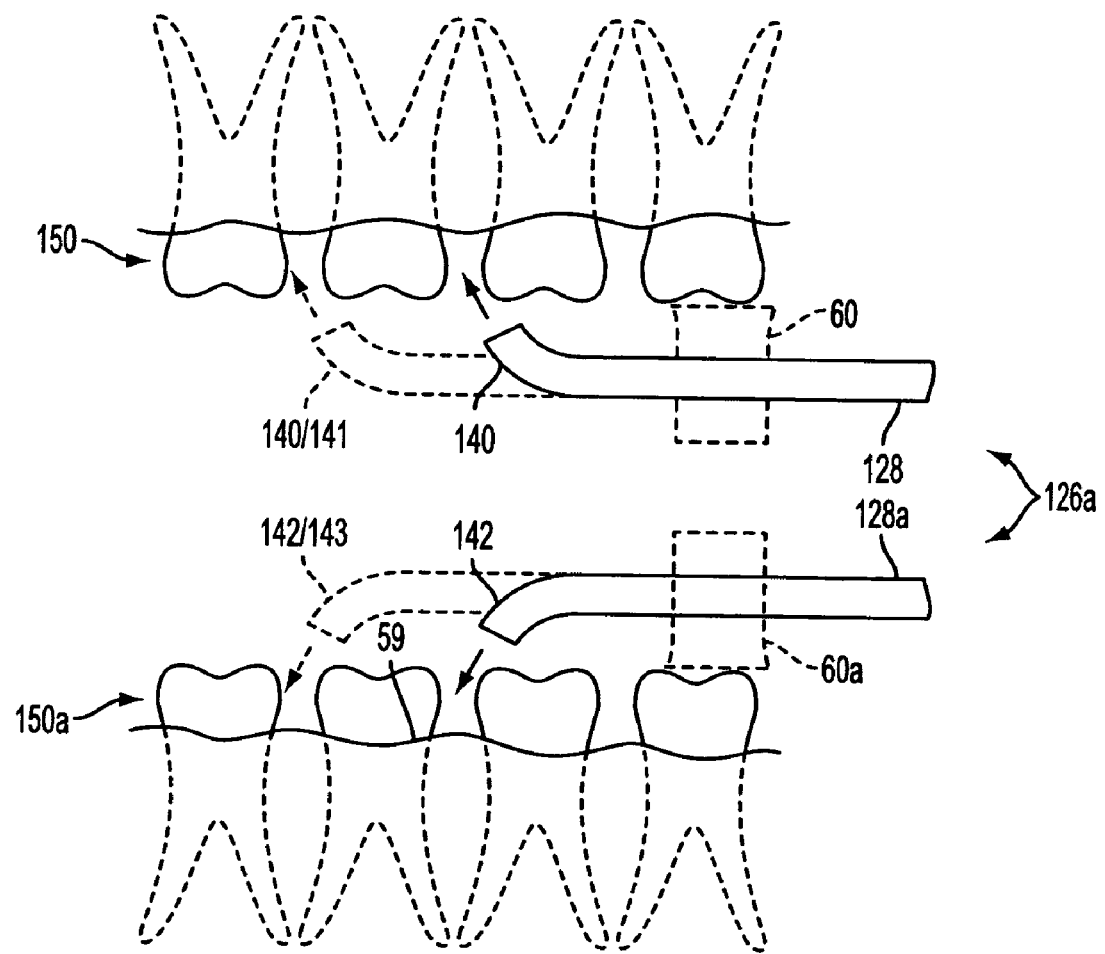
FIG. 20A is a side view of an alternative oral hygiene device like that in FIG. 20.

A similar alternative embodiment is shown in FIG. 20, wherein a handle 125 has a further distinctive irrigation assembly 126a which has four nozzles 140, 141, 142 and 143 on four shafts/arms 128, 128a, 129 and 129a. These nozzles may be alternately reciprocable in a fashion like that described for FIGS. 17–19, although here it may be that first side nozzles 140, 142 may be reciprocated together either substantially simultaneously, yet potentially separately. However, in one embodiment, they may be reciprocated as connected to the same cam follower, e.g., follower 206 (see FIGS. 17–19), and second-side nozzles 141, 143 could then also be reciprocated together in opposing relationship to the first side nozzles 140, 142. Thus, nozzles 141, 143 may be moved separately yet substantially simultaneously and/or may similarly be both connected to the same follower, e.g. follower 207 (FIGS. 17–19). The side view of FIG. 20A shows a version of how this might work. In particular, nozzles 140, 142 are shown spraying jets of water at respective top and bottom rows of teeth 150, 150a at substantially the same penetration into the mouth area. A dashed line representation of nozzles 140/141, 142/143 can represent either the reciprocated further penetration of the nozzles 140, 142, or could represent the opposing side nozzles 141, 143 as reciprocating at alternate depths relative to the primarily shown nozzles 140, 142. Note, also shown in dashed lines are optional guide members 60, 60a which could be used to set the relative spacing of the teeth (here, top to bottom) to better orient the nozzles so they are accurately directed at the gum lines (see e.g., gum line 59). Lateral guide members (not shown) could also be used, as could toothbrush members (see below) for this or a like purpose.

Note, different combinations (not shown) may also be had where for example the two top nozzle heads 140, 141 may be reciprocated together and the other, lower two heads 142, 143 may be reciprocated together in opposed relationship to the upper heads. Note, also shown in FIG. 20 is a schematic representation of a pump module 22 with a power unit 38 and a power cable 39 connected thereto, and also, emanating from module 22 is a supply conduit 36 and a power cable 39c which may as shown in dashed lines also emanate from module 22 or may come more directly from the power unit 38.

It may be preferable in various of these reciprocal moving part embodiments to have respective opposing parts moving contrary to each other to provide balance to the overall device. As an example, in any two opposed nozzle orientations (see FIGS. 10, 11 and 17, 18, inter alia), the opposing nozzles may preferably move in opposite directions, one out while the other is moving in and vice versa. Also in four nozzle embodiments, though two such nozzles may move together, it may be preferable to have two move one way while the other two move contrary thereto. This would likely hold true for contrary side versus side movements, as well as it would for relative top and bottom movements.

Figure 21:
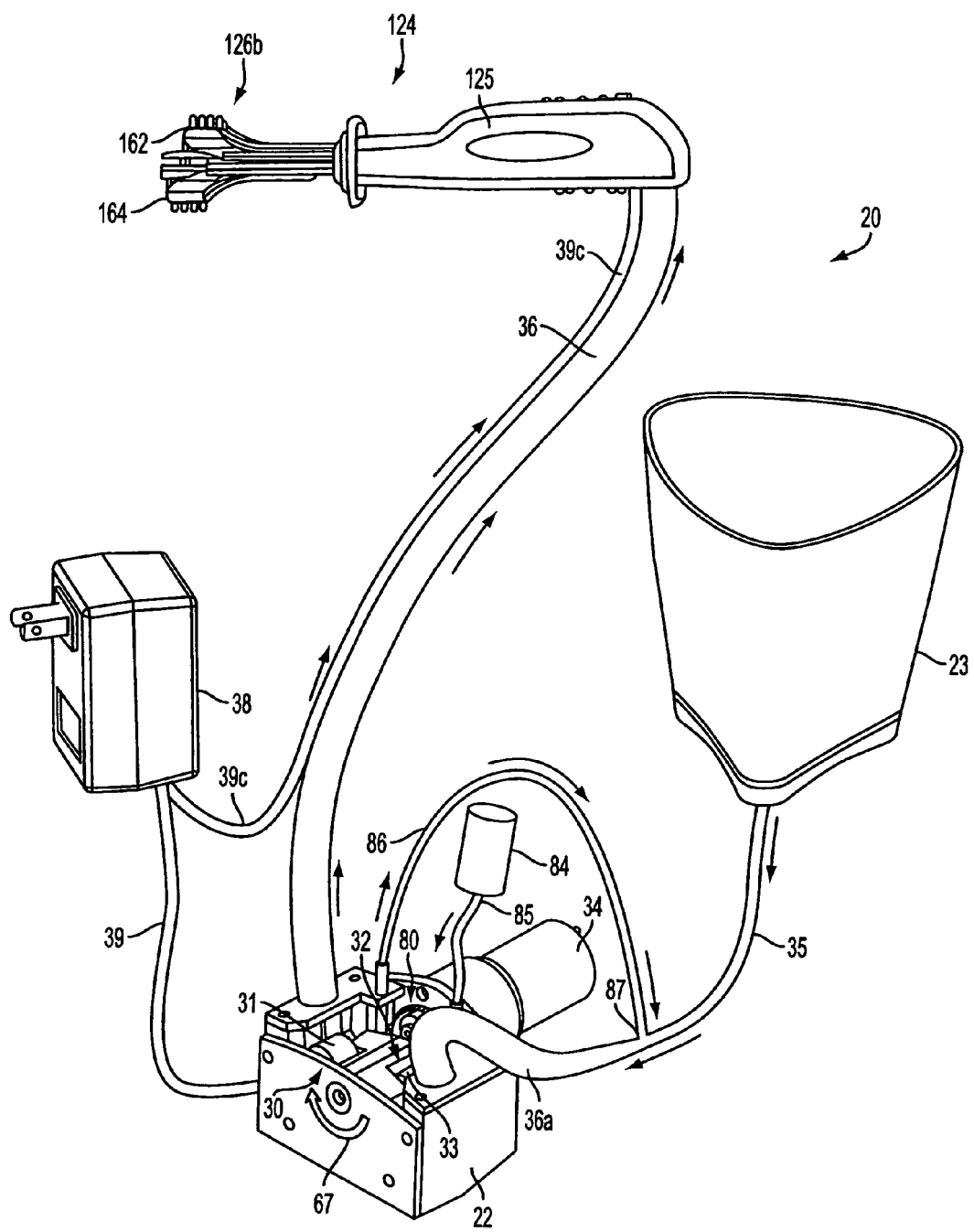
FIG. 21 is an isometric view of an alternative oral hygiene device like that in FIG. 20 also according to the present invention.
Figure 22:
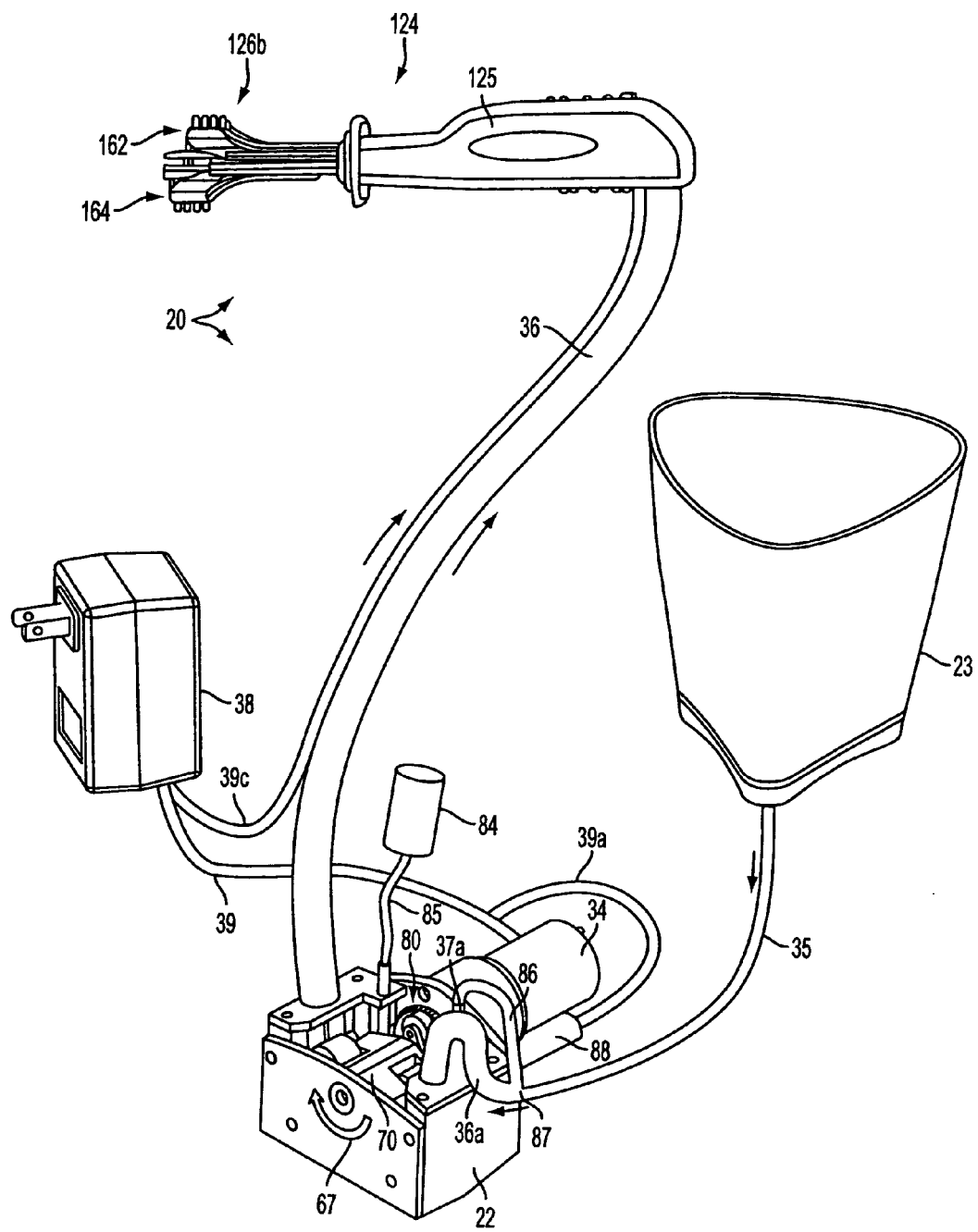
FIG. 22 is a schematic view of a pump alternative which may be used with the oral hygiene devices of FIGS. 20 and 21.

FIGS. 21 and 22 show further variations of these types of combinations with a singular supply line 36 combined with a power line 39c running to the handle 125. FIG. 21 includes a dentifrice pump mechanism 80 run in relative tandem (even if stepped down) with the main pump motor 34, whereas FIG. 22 shows the separate dentifrice pump 88 in fashion as described hereinabove. Note, various pump alternatives might be used herewith as well, such as piston driven injection pumps (see FIGS. 7–8, though utilizing only one chamber, or having both chambers feed one delivery line 36). Further note however, that two alternative brush head assemblies 162, 164 are also shown in FIGS. 21, 22, which could, as described below, be used with any of the herein described oral irrigation alternatives.

Figure 23:
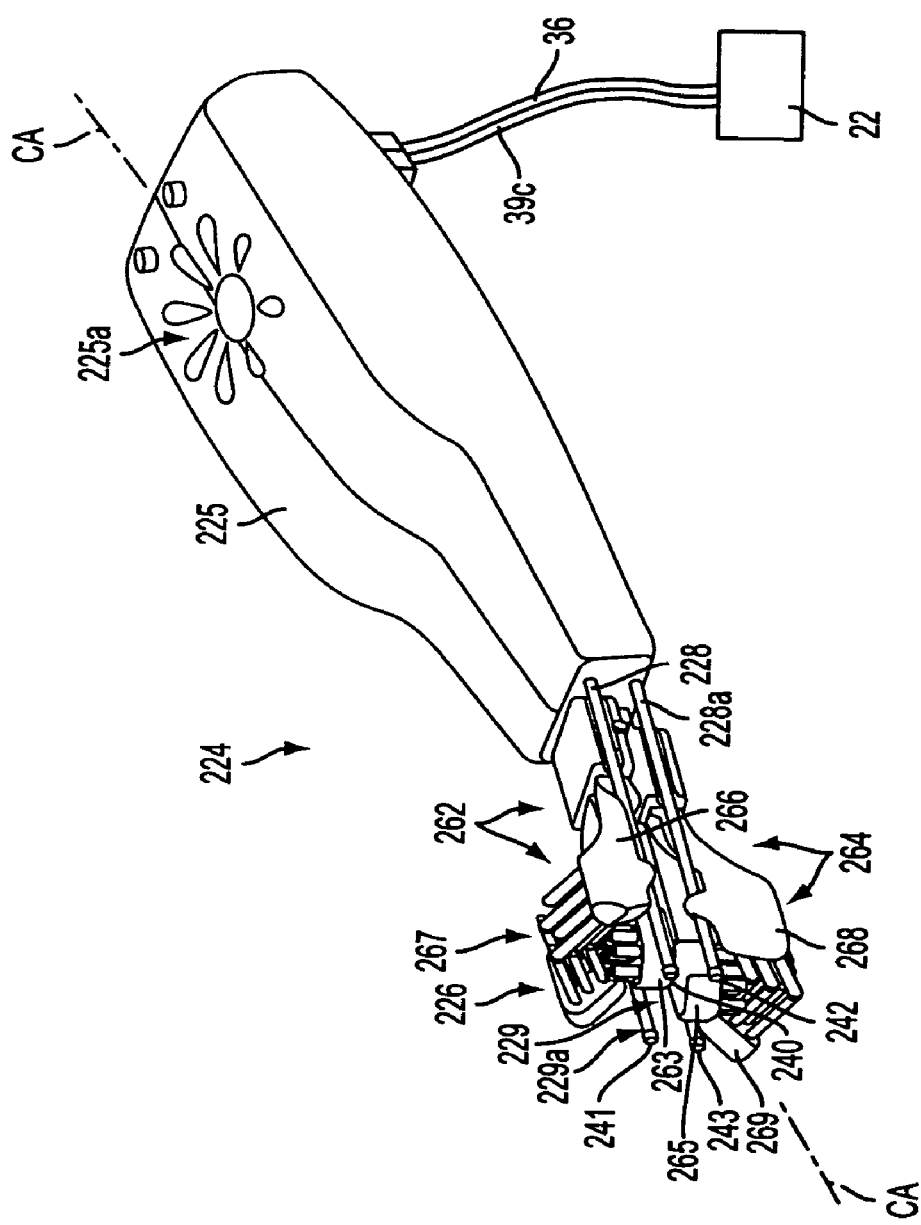
FIG. 23 is an isometric schematic view of an alternative oral hygiene device according to the present invention.
Figure 24:
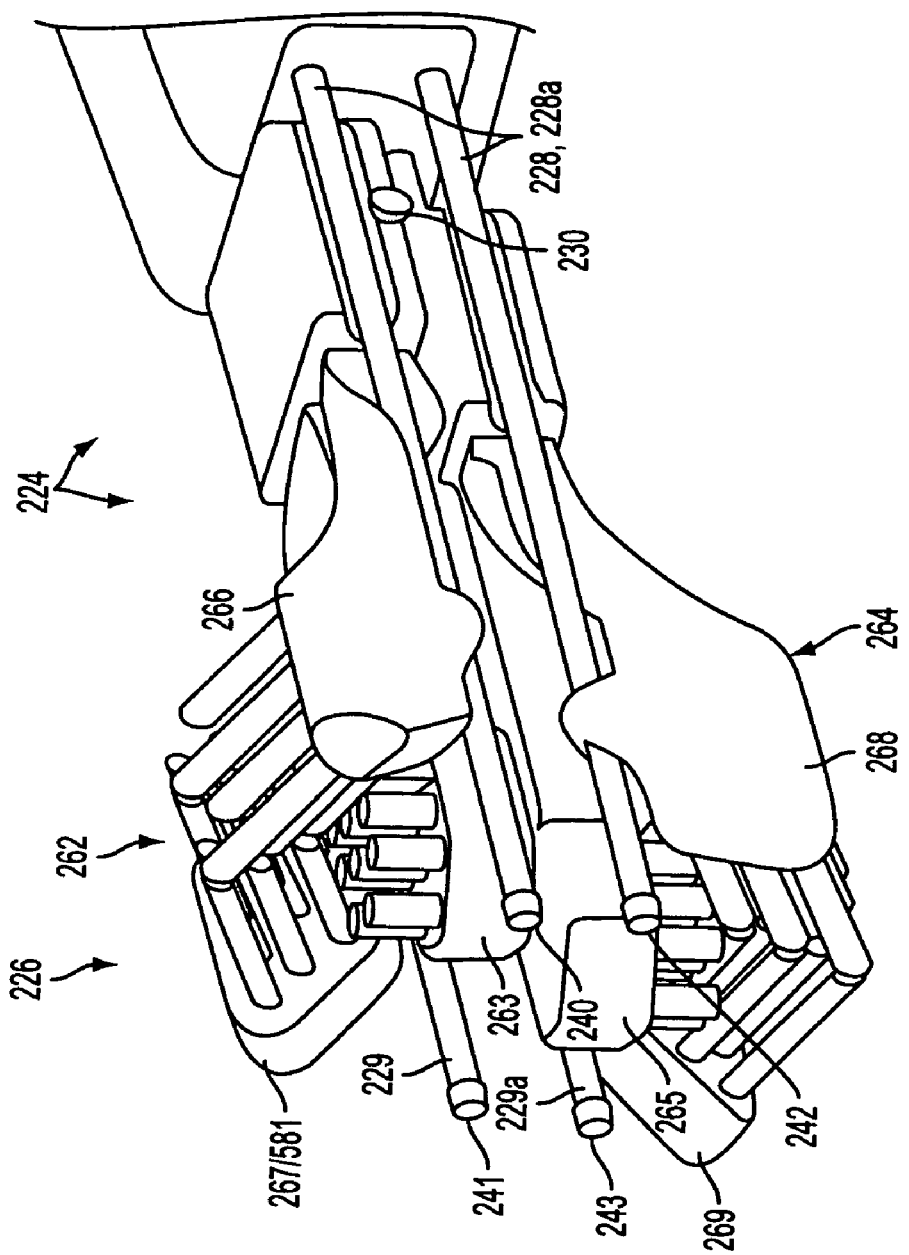
FIG. 24 is an enlarged broken-away isometric view of an oral hygiene device like that in FIG. 23.
Figure 25:
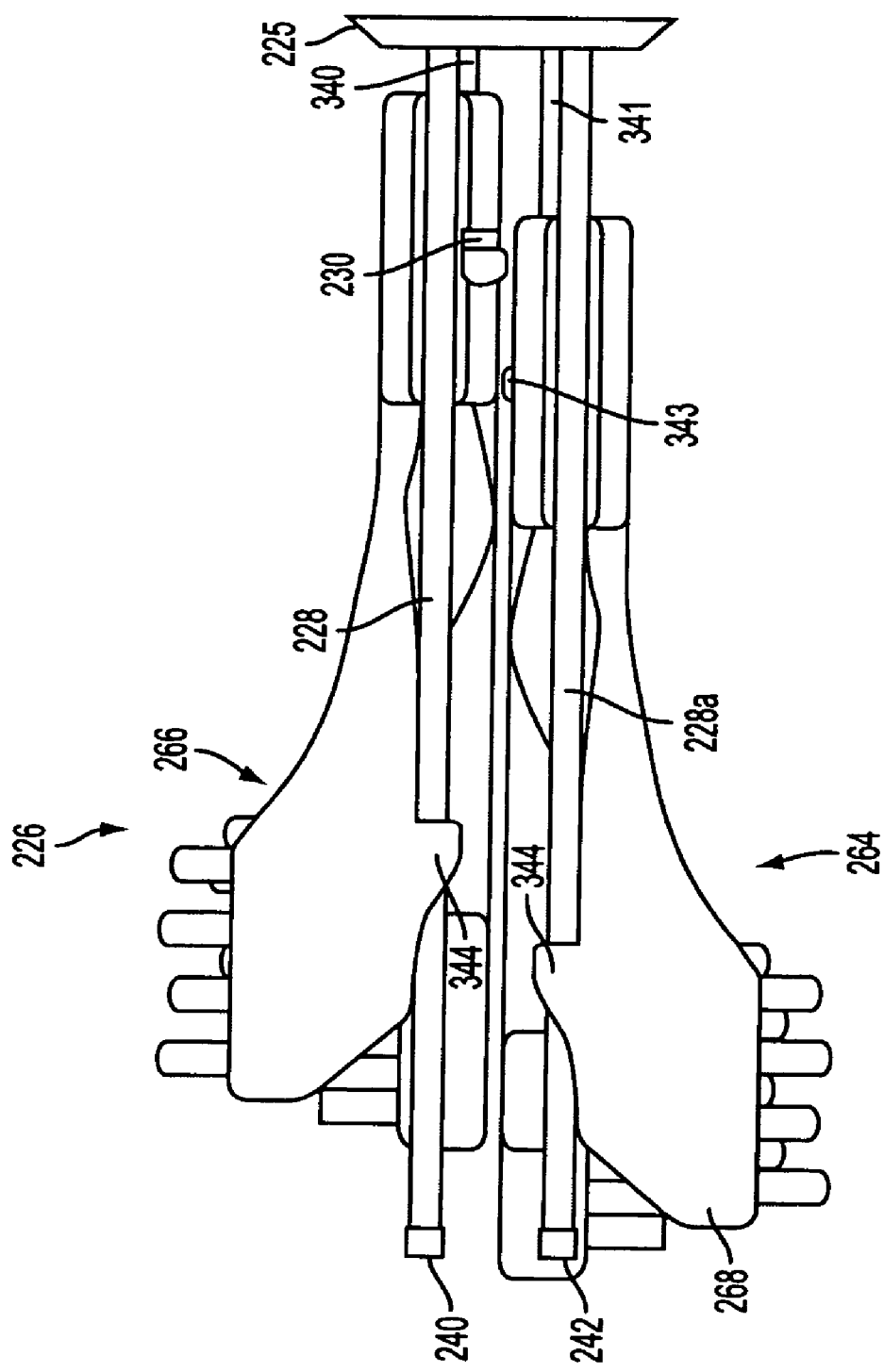
FIG. 25 is an elevational view of a cut-away portion of an oral hygiene device like that in FIG. 23.
Figure 26:
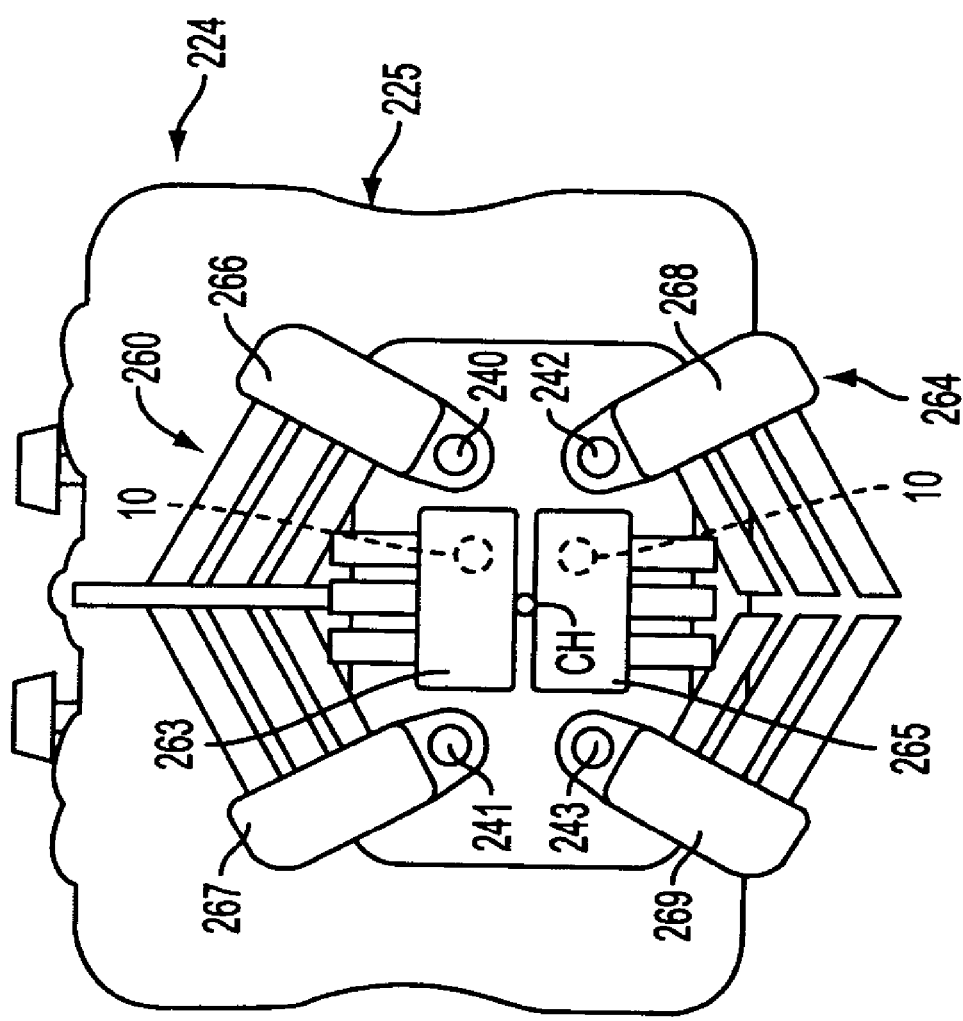
FIG. 26 is a frontal elevational view of an oral hygiene device like that in FIG. 23.
Figure 27:
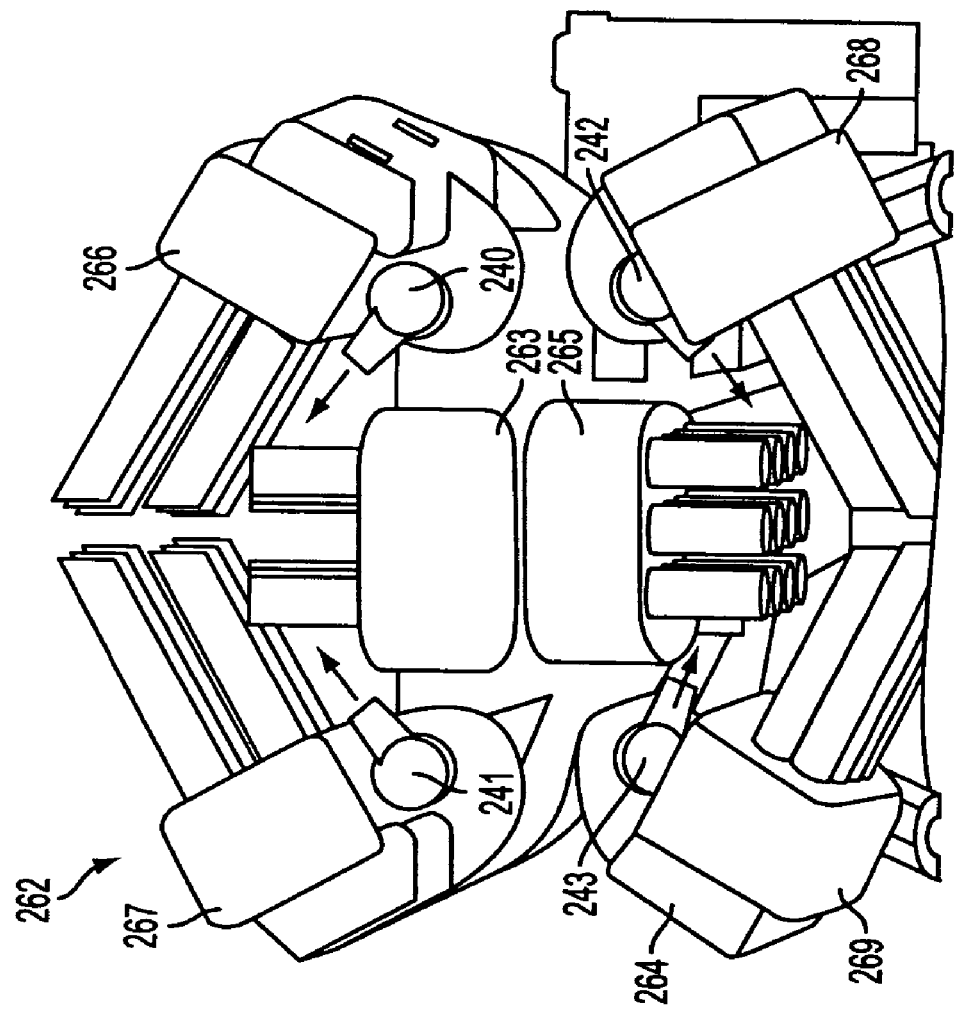
FIG. 27 is an enlarged frontal elevational view of an oral hygiene device like that in FIGS. 23 and 26.
Figure 28:
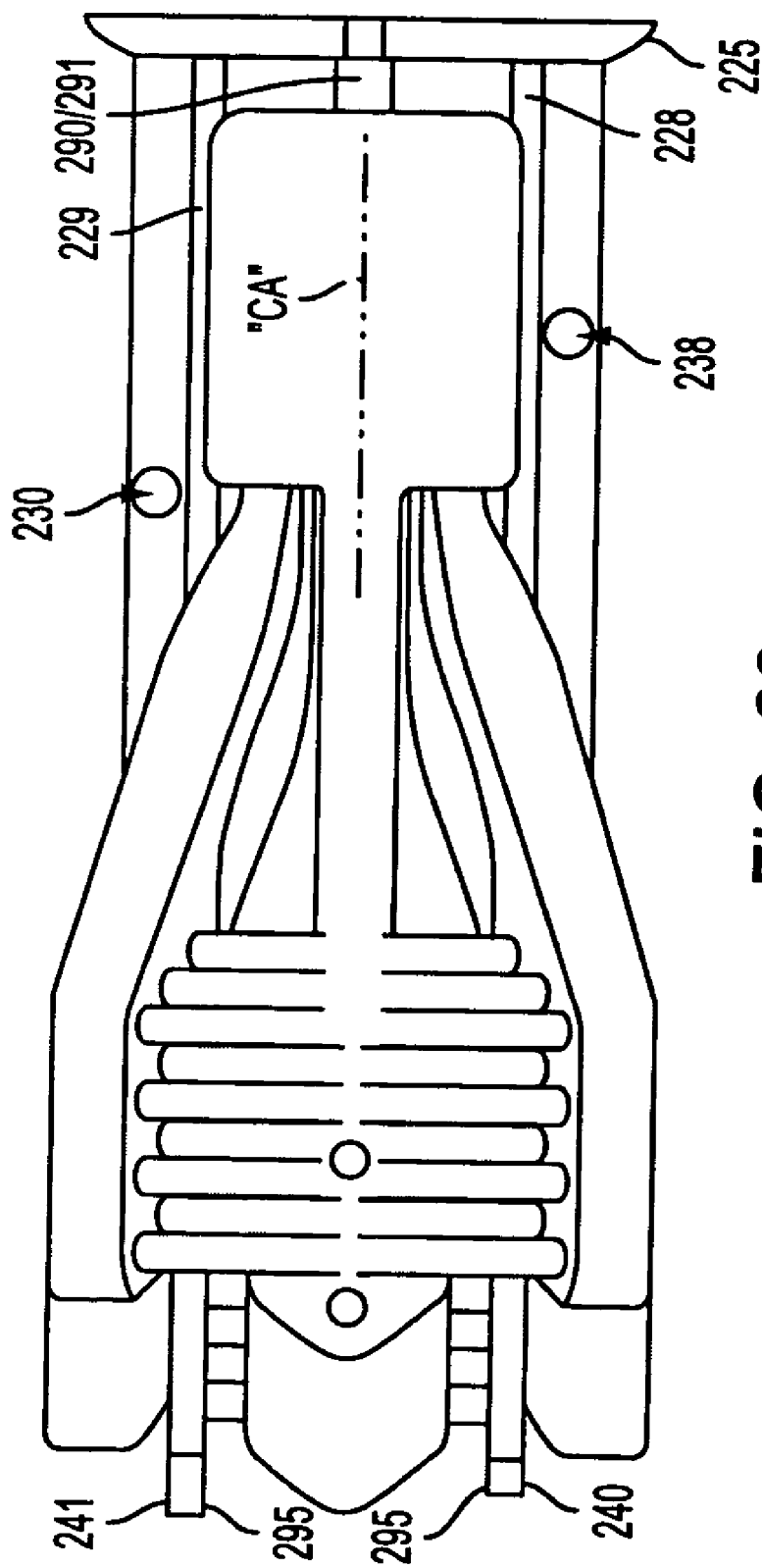
FIG. 28 is a top plan view of a cut-away portion of an oral hygiene device like that in FIG. 23.

More particularly, also disclosed herein are various toothbrush alternative (powered and stationary) with and without oral irrigation alternatives. In a first example, shown generally in FIGS. 23 through 28, a brush and/or irrigation assembly 224 may include a handle 225 extending along a central axis (CA) and including therealong: a rearwardly positioned control portion 225a of the handle 225; and a forwardly positioned brushing assembly 226 including at least one, and preferably two tripartite brushing heads 262, 264 spaced in opposing above and below directions away from said central axis. Each of said tripartite brush head assemblies 262, 264 may respectively headwise include respective principal crown surface brush heads 263, 265 and optionally also pairs of laterally opposed brush heads 266, 267 and 268, 269 for brushing lingual and bucal surfaces and occlussional surfaces of a row of teeth. In many embodiments, the control handle 225 may be provided with conduit means (see e.g., supply conduit 36 from pump module 22) adapted to deliver irrigation water adjacent or into and/or through said one or two or more stationary or longitudinally movable cleaning head assemblies (see below). Jet ports 240, 241, 242 and/or 243 may thus also be provided on arms 228, 228a, 229, and/or 229a for oral irrigation. As introduced, the control handle may in some embodiments be provided with powering means (see e.g., power line 39c in FIG. 23) for providing reciprocating longitudinal movement in synchronization of the nozzle assemblies of ports 240, 241, 242 and/or 243 and/or the tripartite brushing head assemblies 262, 264.

An assembly such as this may be adequate for twin cooperative goals of efficaciously brushing the occlusial and lingual-bucal surfaces (including gaps therebetween) while also simultaneously irrigating the aforementioned surfaces and also the underlying teeth gums. An aspect hereof may thus be the provision of improved powered toothbrush augmented with oral irrigation for simultaneously efficaciously brushing the occlusial and the lingual bucal surfaces including any gaps therebetween while simultaneously beneficially irrigating the teeth surfaces and also the underlying teeth gums, the latter benefit representing therapeutical prevention of periodontal problems.

In a first of these alternative embodiments, the one or more brush head assemblies 262 and/or 264 may be disposed in substantially stationary relationship relative to the handle 225, and the nozzles 240–243 may also be stationary. Or, in a next embodiment, the brush head assemblies may be substantially stationary and the nozzles and arms 228, 228a, 229 and/or 229a may be made substantially reciprocal in any of several fashions such as some of those embodiments described in more detail above (see FIGS. 17–19, inter alia). Particularly in an example such as those shown in FIGS. 23–28, the arms 228, 228a, 229 and/or 229a may be disposed outside and/or otherwise adjacent the brush head assemblies 262, 264 and thus reciprocate therealong. As shown in more detail in FIGS. 25 and 28, the arms 228, 228a, 229 and/or 229a may thus run along and/or may actually run in grooves or other structural manifestations in the brush bodies 343 and may thus be merely adjacent or actually be in some contact with the brush bodies 343. A clip 230 (see FIG. 24) may assist in securing this/these positioning(s). Note, as described thus far, the brush heads and bodies are substantially stationary and may be connected to the handle 225 by respective structural shafts 340, 341 (see FIGS. 25 and 28). One or more further structural wrap-around catch(es) 344 (see FIGS. 24 and 25) may also optionally be used to position the shaft arms 228, 228a, 229 and/or 229a relative to the brush bodies 343 whether either is moving relative to the other.

In this and various of the other toothbrush examples herein, particularly with tripartite brushheads, the brushhead assembly or assemblies 262, 264 may be adapted to receive one or more teeth securely therein, and thereby position the device 224 such that the nozzles 240–243 may be very advantageously aimed at the teeth and/or gums in strategic position to provide maximal cleaning. An angle of such cleaning may be such as to point the nozzles at the gum line as suggested by various drawing figures herein, as for example FIG. 20A. Thus the brush heads could provide the service suggested for the guide members 60, and/or 60a therein.

Brush head assemblies could include one or more brush heads, as for example as shown wherein a tripartite assembly 262 could include a crown brush 263, and could optionally further include one or more laterally space heads 266, 267. Similarly, a lower tripartite assembly 264 could include a crown brush 265, and optional further lateral heads 268, 269. In such embodiments, the brush head assemblies could provide very secure top to bottom and lateral, side to side positioning of the cleaning assembly 226 inside a user's mouth. All the user need do is bite down into the brush head assembly(ies), and thereby have the brushes and nozzles adequately and potentially very accurately positioned for maximal cleaning.

In another embodiment also illustrated by the drawings of FIGS. 23–28, the arms and nozzles may be disposed in a substantially stationary disposition and the brush heads 262, 264 made to move in reciprocal in and out fashion. Generically, this would describe a power toothbrush with oral irrigation device 224 of the present invention which may be further described as extending along a longitudinal and in one embodiment preferably horizontal central axis and include a rearwardly positioned control handle 225 extending along the central axis; and forwardly positioned of and in longitudinally reciprocatable relationship to said control handle, a cleaning head assembly 226 having at least one tripartite brushing head 262 that may be vertically spaced away from a central axis. The tripartite brushing head assembly 262 may include, as above, a first crown brush 263 for brushing the occlusial surfaces of a row of teeth and may also include lateral and opposed second and third angularly disposed brushes 266, 267 for brushing lingual and bucal surfaces of the row of teeth that may be interposable between the upright second brush and third brush. In the embodiments wherein the brush assemblies are disposed in substantially horizontal orientation, the crown brush will be substantially horizontal, and the lateral brushes upright standing from the horizontal. The control handle 225 may here also be internally or externally provided with powering means for effecting a longitudinally reciprocatable relationship of the at least one tripartite brushing head; and the control handle may further be provided with internal and/or external conduit means adapted to deliver irrigation water into and/or adjacent said tripartite brushing head(s).

More particularly, the powered toothbrush with oral irrigation as hereabove described may be especially adaptable for simultaneously reliably brushing the user's upper row of teeth and the lower row of teeth and whereby there may be on opposite sides vertically from a central axis both an upper and also a lower tripartite brushing head assembly 262, 264; wherein the control-handle powering means may be adapted to cause such brushing heads to simultaneously longitudinally reciprocate in opposite directions; and wherein the control-handle conduit means is adapted to simultaneously deliver water into and/or adjacent both said tripartite brushing heads via the nozzles 240, 241, 242 and/or 243.

Thus as shown in the drawings, a representative embodiment 224 of the present invention may include a powered toothbrush with oral irrigation and/or a powered oral irrigation device with a toothbrush. This device 224 extends longitudinally (and in one orientation, horizontally) along a central axis CA and has four main parts including: a rearwardly positioned control-handle 225; at least one forwardly positioned tripartite brushing head(s) 262 and/or 264 vertically spaced form the central axis CA and directionally longitudinally reciprocatably attached to the handle 225. Each such longitudinal reciprocatable tripartite brushing head includes a horizontal brush 263, 265 for brushing the occlusial surfaces of a row of teeth, and opposed upright second brushes 266, 267 and/or 268, 269 for respectively simultaneously brushing lingual and bucal surfaces of upright brushes surrounded teeth-row; the control handle 225 being internally or externally provided with powering means (see e.g., power cord 39c for external supply, an internal battery (not shown) could be alternated therefor), for effecting longitudinal reciprocation of at least one said brush head 262 and/or 264; and the control-handle 225 being provided with a conduit or conduits 36 for delivering irrigation water into one or both reciprocatable tripartite brushing heads 262 and/or 264.

In the detailed FIGS. 24–28 are shown isometric, side and front elevational and top plan views of the representative embodiment 224. Referring now to these details, a control-handle 225 with two tripartite brush head assemblies 262, 264 reciprocatably attached thereto. Brush head assemblies 262, 264 can simultaneously brush an upper row of teeth and a lower row of teeth. The brush heads may in one embodiment, reciprocate in and out about ¼ inch of movement. The upper brush head and lower brush head may preferably be made to move in opposite directions, i.e., when the upper brush head 262 is moving inward, the lower brush head 264 is moving outward. This is desirable in many embodiments because when a user bites into the upper and lower brush heads at the same time, the opposing reciprocatable movement can provide a "balance" so that the power handle does not tend to move in and out as a result of contact with both the upper and lower brush head simultaneously.

One, two, or as shown in FIGS. 23–28, four (or any other practical number of) water delivery tubes or conduits 228, 228a, 229, and/or 229a may be rigidly or movably attached to the end of the handle 225. Again, as described in some embodiments these tubes can be made to be non-reciprocatable. However, these may in alternative embodiments be made movable for the alternative reasons further described relative to FIGS. 10–17 inter alia. Water jet spray nozzles/orifices 240, 241, 242 and 243 may be disposed at the respective ends of the tubes 228, 228a, 229 and/or 229a, and these nozzles/orifices may be directed toward the user's gum line and direct water jet flow between the teeth. One or two (or more) water tubes 36 (and/or 37, see FIGS. 1–9) may then be connected to the delivery tubes 228, 228a, 229 and/or 229a, directly or through respective Y-connections, and this/these tubes 36, 37 may then run from their attachment to the power handle down to the control module 22. As described, a water pump of one or more of a variety of types (peristaltic or piston or otherwise) may be used to pressurize water for delivery into and through the tube or tubes 36, 37 in either a pulsating or a relative continuous streaming fashion. In many embodiments, this may include delivery into and through first one tube, then the other to provide alternating pulsating water jets.

Thus, either movable nozzles or movable brushes or both simultaneously reciprocating may be found in devices of the present invention. Again, other guide members not involving brush heads (see FIG. 20A) whether of up and down guides or lateral guides or both may be included herein.

Moreover, the movements of the nozzles and/or brush heads may be forced by various mechanisms, but could include mechanisms such as those shown and described relative to FIGS. 17–18, inter alia. Thus, inside the control handle 225 maybe a direct current (DC) motor that may provide primary power to reciprocate the brush heads 262, 264. The heart of this double reciprocal/opposing movement could thus be a gear with a cam on both sides of the gear. The upper cam, spur gear, and lower cam could here also all be combined as one piece. The structural shafts may then be attached to the cam followers within the power handle 225. When the DC motor runs, its pinion gear could then turn a crown gear which may be attached to small spur gear which in turn may be in contact with the double-cam big spur gear. This double-cam spur gear could then move two cam followers in and out relative to the power handle thus causing the structural shafts to reciprocate in opposing directions.

The respective brush head assembly(ies) 262, 264 can also be detachably attached to the end of the respective structural brush shafts 340, 341. Detachability may be effected through use of depressible button 230 which can release a spring catch (not shown), and the respective brush head 262 (and/or 264) can then be removed or pulled therefrom. A similar disposition and action may be had with the nozzles (if so desired) and the corresponding structural shaft arms. In some embodiments, the brush head(s) (or replaceable nozzles) may be installed onto corresponding shafts, until they go on to a point at which the button "snaps" and locks the brush head (or nozzle) in relation to the respective structural shaft.

Figure 29A:
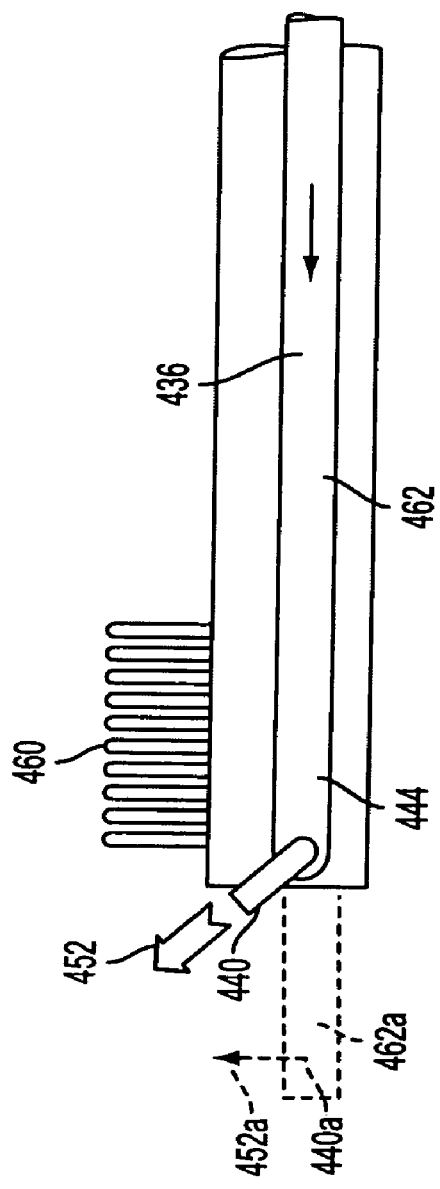
FIG. 29A is an enlarged broken-away side elevational view of an alternative oral hygiene device according to an embodiment of the present invention.
Figure 29B:
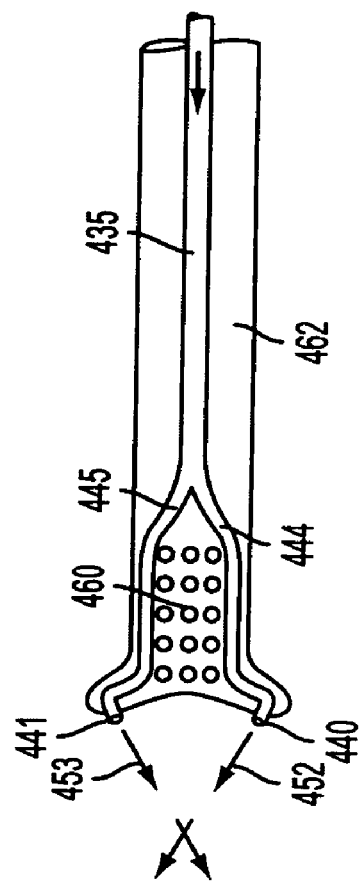
FIG. 29B is a top plan view of a broken-away portion of an oral hygiene device like that in FIG. 29A.

In the next FIGS. 29A and 29B, there is a depiction of a side view of a brush head 460 having the oral irrigation tube 436 disposed therein. The brush and nozzle(s) may be stationary or reciprocate as above, however, here they will reciprocate together. Top and bottom brushes (not shown) with or without lateral brushes (not shown) may also be used herewith. Tube 436 extends along and within the structural shaft 462 of brush 460, and then the tube splits into tube portions 444, 445 which ultimately deliver fluid to the nozzles 440, 441. The fluid jets 452, 453 may be directed angularly as shown. This may provide the pattern of jetting (or streaming) shown; however, this may be advantageous in that there will likely be no adverse interaction of the jets with the brush head as may have been the case with disparate jet nozzles and brush heads as shown in FIG. 29A by the dashed line version of nozzle 440a on structure 462a which issues a jet 452a which could interact with a moving brush 460. Again, one or more of these brushes may be disposed in reciprocal motive disposition in and relative to a control handle 125/225. Also, when the water tubes pass through and/or emanate from the brush structure through a hole in or adjacent the brushes, the tube and/or nozzles have enough clearance to issue jets or streams without interacting or otherwise interfering with the brush head reciprocating along the user's tooth and/or gum line.

From the foregoing, it is readily apparent that new and useful embodiments of the present invention have been herein described and illustrated which fulfill numerous desiderata in remarkably unexpected fashions. It is, of course, understood that such modifications, alterations and adaptations as may readily occur to the artisan confronted with this disclosure are intended within the spirit of this disclosure which is limited only by the scope of the claims appended hereto.

What is claimed is:

1. A device for oral hygiene comprising:
   an oral irrigation device including an irrigation handle having first and second nozzles and in which said handle has first and second fluid connections defined therein in fluid communication with said first and second nozzles;
   first and second flexible tube portions; and
   a fluid source connected to said oral irrigation device, said first and second fluid connections and said first and second nozzles via said first and second flexible tube portions, each of said first and second flexible tube portions being in fluid communication with a respective one of said first and second nozzles;
   a peristaltic pump module having first and second pump raceways and first and second rollers;
   whereby said first flexible tube portion is adapted to be disposed in said first pump raceway, said first roller being adapted to run in said first raceway and obstruct said first tube portion therein, said second flexible tube portion being adapted to be disposed in said second pump raceway, said second roller being adapted to run in said second raceway and obstruct said second tube portion therein; and
   whereby said first and second rollers are disposed to rotate in said raceways and thereby move the corresponding first and second obstructions along the first and second flexible tubing portions.

2. A device according to claim 1, in which said first and second nozzles are disposed in generally opposing relationship to each other.

3. A device according to claim 1, in which each of said first and second nozzles is disposed at a discrete angle relative to each other.

4. A device according to claim 1, in which each of said first and second nozzles is disposed at a discrete angle relative to an oral cavity feature.

5. A device according to claim 4, in which said oral cavity feature is a gum line intersection of a tooth and gums.

6. A device according to claim 1, in which said oral irrigation device has a guide member connected thereto.

7. A device according to claim 6, in which said guide member is a bite block.

8. A device according to claim 1, in which said oral irrigation device has a tooth brush connected thereto.

9. A device according to claim 1, in which said oral irrigation device has an arrangement of tooth brushes connected thereto.

10. A device for oral hygiene comprising:
- an oral irrigation device including an irrigation handle having a first nozzle and a second nozzle and in which said handle has first and second fluid connections defined therein in fluid communication with said first and second nozzles;
- first and second flexible tube portions, and
- a fluid source connected to said oral irrigation device and said first and second nozzles via said first and second flexible tube portions, each of said first and second flexible tube portions being connected in fluid communication to a respective one of said first and second nozzles;
- a peristaltic pump module having first and second pump raceways and first and second rollers;
- whereby said firs flexible tube portion is adapted to be disposed in said first pump raceway, said first roller being adapted to run in said first raceway and obstruct said first tube portion therein, said second flexible tube portion being adapted to be disposed in said second pump raceway, said second roller being adapted to run in said second raceway and obstruct said second tube portion therein; and
- whereby said first end second rollers are disposed to rotate in said raceways and thereby move the corresponding first and second obstructions along the first and second flexible tubing portions; and
- whereby said first and second rollers are offset one from each other so that the first and second rollers move the corresponding first and second obstruction at alternative intervals.

11. A device for oral hygiene comprising:
- an oral irrigation device including an irrigation handle having first and second nozzles and in which said handle has first and second fluid connections defined therein in fluid communication with said first and second nozzles, and said irrigation handle having a toothbrush connected thereto;
- first and second flexible tube portions and a fluid source connected to said oral irrigation device and said first and second nozzles via said first and second flexible tube portions, each of said first and second flexible tube portions being connected in fluid communication to a respective one of said first and second nozzles;
- a peristaltic pump module having first and second pump raceways and first and second rollers;
- whereby said first flexible tube portion is adapted to be disposed in said first pump raceway, said first roller being adapted to run in said first raceway and obstruct said first tube portion therein, said second flexible tube portion being adapted to be disposed in said second pump raceway, said second roller being adapted to run in said second raceway and obstruct said second tube portion therein; and
- whereby said first and second rollers are disposed to rotate in said raceways and thereby move the corresponding first and second obstructions along the first and second flexible tubing portions; and
- whereby said first and second rollers are offset one from each other so that the first and second rollers move the corresponding first and second obstruction at alternative intervals.

12. A device according to claim 11, in which said oral irrigation device has an arrangement of tooth brushes connected thereto.

13. A device according to claim 11, in which said nozzles are movable relative to said toothbrush.

14. A device according to claim 11, in which said oral irrigation device has an arrangement of tooth brushes connected thereto, and in which said nozzles are movable relative to said toothbrushes.

15. A device according to claim 11, in which said toothbrush is movable with said nozzles.

16. A device according to claim 11, in which said oral irrigation device has an arrangement of tooth brushes connected thereto, and in which said toothbrushes are movable with said nozzles.

* * * * *